US007288617B2

(12) United States Patent
Treacher et al.

(10) Patent No.: US 7,288,617 B2
(45) Date of Patent: *Oct. 30, 2007

(54) CONJUGATED POLYMERS CONTAINING SPIROBIFLUORENE UNITS AND FLUORENE UNITS, AND THE USE THEREOF

(75) Inventors: Kevin Treacher, Kelkcheim/Munster (DE); Heinrich Becker, Glashütten (DE); Philipp Stossel, Frankfurt (DE); Hubert Spreitzer, Viernheim (DE); Aurelie Falcou, Mainz (DE); Amir Parham, Frankfurt (DE); Arne Busing, Frankfurt (DE)

(73) Assignee: Merck Patent GmbH (DE)

( * ) Notice: Subject to any disclaimer, the term of this patent is extended or adjusted under 35 U.S.C. 154(b) by 143 days.

This patent is subject to a terminal disclaimer.

(21) Appl. No.: 10/472,736

(22) PCT Filed: Mar. 22, 2002

(86) PCT No.: PCT/EP02/03221

§ 371 (c)(1),
(2), (4) Date: Dec. 15, 2003

(87) PCT Pub. No.: WO02/077060

PCT Pub. Date: Oct. 3, 2002

(65) Prior Publication Data

US 2004/0135131 A1 Jul. 15, 2004

(30) Foreign Application Priority Data

Mar. 24, 2001 (DE) ................................. 101 14 477

(51) Int. Cl.
C08G 61/02 (2006.01)
C08G 61/12 (2006.01)

(52) U.S. Cl. .................. 528/86; 528/397; 528/422; 428/690; 428/917; 252/582; 259/E51.085; 259/E51.051

(58) Field of Classification Search ............... 528/86, 528/397, 422; 428/690, 917; 252/582; 257/E51.085, 257/E51.051
See application file for complete search history.

(56) References Cited

U.S. PATENT DOCUMENTS

| 5,621,131 | A | 4/1997 | Kreuder et al. |
| 5,763,636 | A * | 6/1998 | Kreuder et al. ............... 558/46 |
| 5,840,217 | A | 11/1998 | Lupo et al. |
| 6,353,083 | B1 | 3/2002 | Inbasekaran et al. |
| 6,541,602 | B1 * | 4/2003 | Spreitzer et al. ........... 528/394 |

FOREIGN PATENT DOCUMENTS

| EP | 0676461 A2 | 10/1995 |
| EP | 0676461 A3 | 10/1995 |
| EP | 0707020 A2 | 4/1996 |
| EP | 1138746 | 10/2001 |
| WO | WO-00/46321 | 8/2000 |

OTHER PUBLICATIONS

Yu et al, Spiro-functionalized polyfluorene derivatives as blue light emitting materials, Wiley-VCH Verag GmbH, 2000, Chem Abstract 134: 87131.*
U.S. Appl. 10/488,625 claims.*
Wang-Lin Yu, et al, "Spiro-Functionalized Polyfluorene Derivatives as Blue Light-Emitting Materials," Advanced Materials 12; 828-831, XP-002209789, (2000).

* cited by examiner

Primary Examiner—Duc Truong
(74) Attorney, Agent, or Firm—Connolly Bove Lodge & Hutz LLP

(57) ABSTRACT

The present invention relates to novel polymers which comprise spirobifluorene and fluorine units of the formulae (I) and (II) and may further comprise additional structural elements which may have charge transport properties, hole transport properties and/or electron transport properties.

Such materials display a significantly improved property profile in electronic components, particularly when used in a PLED, in particular as electroluminescence material, in organic integrated circuits (O-ICs), organic field effect transistors (OFETs), organic thin film transistors (OTFTs), organic solar cells (O-SCs) or organic laser diodes (O lasers).

34 Claims, No Drawings

CONJUGATED POLYMERS CONTAINING SPIROBIFLUORENE UNITS AND FLUORENE UNITS, AND THE USE THEREOF

Wide-ranging research on the commercialization of display and lighting elements based on polymeric (organic) light-emitting diodes (PLEDs) has been pursued for about 10 years. This development was triggered by the fundamental developments disclosed in EP 423 283 (WO 90/13148). In contrast to low molecular weight organic light-emitting diodes (OLEDs) which have already been introduced on the market, e.g. commercially available car radios having an "organic display" from Pioneer, the PLEDs have not yet been commercialized. Significant improvements are still necessary in order to make these displays genuinely competitive with or superior to the liquid crystal displays (LCDs) which currently dominate the market.

EPD-A-0 423 283, EP-A-0 443 861, WO 98/27136, EP-A-1 025 183 and WO 99/24526 disclose polyarylenevinylene derivatives as conjugated polymeric emitters.

EP-A-0 842 208, WO 99/54385, WO 00/22027, WO 00/22026 and WO 00/46321 disclose polyfluorene derivatives as conjugated polymeric emitters.

EP-A-0 707 020 and EP-A-0 894 107 disclose polyspirobifluorene derivatives as conjugated polymeric emitters.

For the purposes of the present invention, conjugated polymers are polymers which have mainly $sp^2$-hybridized carbon atoms, which may also be replaced by appropriate heteroatoms, in the main chain. This is equivalent to the alternate presence of double and single bonds in the main chain. It should be noted that naturally occurring defects which lead to interruptions in the conjugation do not invalidate the term "conjugated polymers". However, polymers which have relatively large numbers of deliberately inserted nonconjugated segments are not encompassed by this definition. Furthermore, polymers which have, for example, arylamine units and/or particular heterocycles (i.e. conjugation via N—, O—, or S atoms) and/or organometallic complexes (i.e. conjugation via the metal atom) in the main chain are likewise considered to be conjugated for the purposes of the present application. On the other hand, units such as simple (thio)ether bridges, ester linkages and amide or imide linkages are clearly defined as nonconjugated segments.

The general structure of PLEDs is described in the abovementioned patent applications and patents and is also explained in more detail below. Further refinements (for example passive matrix addressing, active matrix addressing) are likewise already known, but are not critical for the further description of the present patent application.

The commercialization of both monochrome and full color displays based on PLEDs is being examined at present. While the monochrome displays may be able to be produced by means of simple coating technologies (e.g. doctor blade coating, spin coating), polychrome or full color display elements very probably require the use of printing methods (e.g. inkjet printing, offset printing, gravure printing). However, all these processes require soluble polymers.

Some of the conjugated polymers described in the abovementioned patent applications do display good properties for the uses mentioned.

Important properties include the following:
High luminous and energy efficiency when used in PLEDs.
Long operating life when used in PLEDs.
Low operating voltage.
Good storage stability, both when used in PLEDs and before introduction into corresponding devices.
Good solubility in organic solvents to permit an appropriate coating process.
Sensible availability to make economical use in mass-produced products possible.
Ability to achieve various colors so as to make full color display elements possible.

It has now surprisingly been found that a new class of conjugated polymers has very good properties which are frequently superior to the abovementioned prior art. These polymers and their use in PLEDs are subject matter of the present invention.

The invention provides conjugated polymers comprising units of the formula (I)

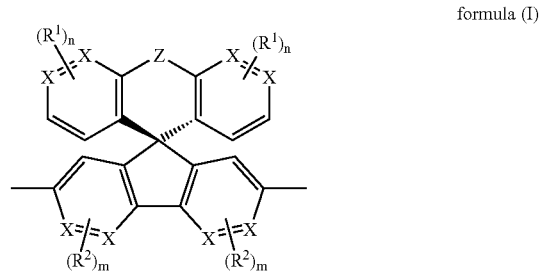

formula (I)

together with units of the formula (II),

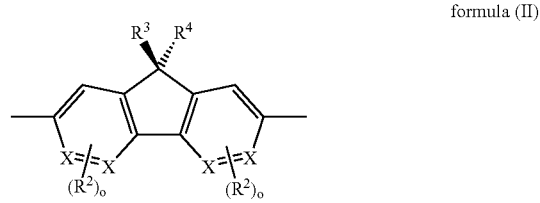

formula (II)

with the proviso that the proportion of repeating units of the formula (I) and formula (II) together make up at least 20%, preferably at least 30%, particularly preferably at least 50%, of all repeating units in the polymer and the ratio of repeating units of the formula (I) to units of the formula (II) is in the range from 1:10 to 10:1, preferably from 1:5 to 5:1, particularly preferably from 1:2 to 2:1, and the symbols and indices have the following meanings:

X is identical or different on each occurrence and is CH, $CR^1$ or N,

Z is identical or different on each occurrence and is a single chemical bond, a $CR^3R^4$ group, a $CR^3R^4$—$CR^3R^4$ group, a $CR^3$=$CR^4$ group, O, S, N—$R^5$, C=O, C=$CR^3R^4$ or $SiR^3R^4$;

$R^1$ is identical or different on each occurrence and is a straight-chain, branched or cyclic alkyl or alkoxy chain which has from 1 to 22 carbon atoms and in which one or more nonadjacent carbon atoms may also be replaced by N—$R^5$, O, S, —CO—O—, O—CO—O, where one or more H atoms may also be replaced by fluorine, an aryl or aryloxy group which has from 5 to 40 carbon atoms and in which one or more carbon atoms may also be replaced by O, S or N and which may also be substituted by one or more nonaromatic radicals $R^1$, or Cl, F, CN, $N(R^5)_2$, where two or more radicals $R^1$ may also be joined to form a ring system;

$R^2$ is identical or different on each occurrence and is a straight-chain, branched or cyclic alkyl or alkoxy chain which has from 1 to 22 carbon atoms and in which one or more nonadjacent carbon atoms may also be replaced by N—$R^5$, O, S, —CO—O—, O—CO—O, where one or more H atoms may also be replaced by fluorine, an aryl or aryloxy group which has from 5 to 40 carbon atoms and in which one or more carbon atoms may also be replaced by O, S or N and which may also be substituted by one or more nonaromatic radicals $R^1$, or CN;

$R^3$, $R^4$ are identical or different on each occurrence and are each H, a straight-chain, branched or cyclic alkyl chain which has from 1 to 22 carbon atoms and in which one or more nonadjacent carbon atoms may also be replaced by N—$R^5$, O, S, —CO—O—, O—CO—O, where one or more H atoms may also be replaced by fluorine, an aryl group which has from 5 to 40 carbon atoms and in which one or more carbon atoms may also be replaced by O, S or N and which may also be substituted by one or more nonaromatic radicals $R^1$, or CN; the two radicals $R^3$ and $R^4$ may also be joined to form a ring which does not, however, lead to structures of the formula (I);

$R^5$ is identical or different on each occurrence and is H, a straight-chain, branched or cyclic alkyl chain which has from 1 to 22 carbon atoms and in which one or more nonadjacent carbon atoms may also be replaced by O, S, —CO—O—, O—CO—O, where one or more H atoms may also be replaced by fluorine, an aryl group which has from 5 to 40 carbon atoms and in which one or more carbon atoms may also be replaced by O, S or N and which may also be substituted by one or more nonaromatic radicals $R^1$;

n is identical or different on each occurrence and is 0, 1, 2, 3 or 4, preferably 0, 1 or 2, particularly preferably 1 or 2;

m is identical or different on each occurrence and is 0, 1, 2 or 3, preferably 0, 1 or 2, particularly preferably 0 or 1;

o is identical or different on each occurrence and is 0, 1, 2 or 3, preferably 0, 1 or 2, particularly preferably 0 or 1, with the proviso that in the case of at least one unit of the formula (I), at least one index n and/or m is not 0.

Even though this is indicated in the description, explicit attention is drawn at this point to the fact that both the structural units of the formula (I) and those of the formula (II) may be unsymmetrically substituted, i.e. different substituents $R^1$ and/or $R^2$ can be present on one unit, or these can be located in different positions on each of the two sides.

The synthesis of the corresponding monomers is comprehensively described in, for example, the abovementioned patent applications and patents.

Thus, for example, monomers which then form structures of the formula (I) in the polymer can be synthesized as described in EP 676.461, EP 707.020, EP 894.107 and the references cited therein.

Furthermore, monomers which then form structures of the formula (II) in the polymer can, for example, be synthesized as described in EP-A-0 842 208, WO 99/54385, WO 00/22026 and the references cited therein.

Compared to the abovementioned polyspirobifluorenes (which comprise units of the formula (I) but not units of the formula (II)) and polyfluorenes (which comprise only units of the formula (II) and not units of the formula (I)), the polymers of the invention have, especially, the following advantages:

(1) It has surprisingly been found that the polymers of the invention (having an otherwise identical or similar structure) display higher luminous efficiencies in use (cf. for example, the data for the polymer P3 according to the invention compared to those for the comparative polymers C1 and C6; analogous comparison of P8 with C2; see examples, table in part B).

This is of tremendous importance since it either allows the same brightness to be achieved at a lower energy consumption, which is particularly important in mobile applications (displays for palmtops, pagers, PDAs, etc.), or enables greater brightnesses to be obtained for the same energy consumption, which can be of interest, for example, for lighting applications.

(2) Furthermore, it has surprisingly been found that, once again in direct comparison, the polymers of the invention display higher operating lives (cf., as above, the data for the polymer P3 according to the invention with those for the comparative polymers C1 and C6; analogous comparison for P8 with C2; see examples, table in part B).

(3) In terms of the solubility behavior (e.g. gelation temperature at a given concentration, viscosity at a given concentration) too, the polymers of the invention are equivalent or superior to the known polymers (cf. for example, the data for the polymer P8 according to the invention with those for the comparative polymer C2; analogous comparison for P1 and P3 with C1 and C6; analogous comparison for P6 with C5; see examples, table in part B).

(4) The availability and achievability of colors when using the polymers of the invention is equivalent to the prior art. Although this is thus not an advantage, the abovementioned advantages under (1) to (3) are not accompanied by an adverse effect, which does frequently occur in technical optimizations.

The polymers of the invention generally have from 10 to 10000, preferably from 50 to 5000, particularly preferably from 50 to 2000, repeating units.

The necessary solubility is ensured by, especially, the substituents $R^1$, $R^3$ and/or $R^4$. If substituents $R^2$ are present, these also contribute to the solubility.

To ensure sufficient solubility, it is necessary for an average of at least 2 nonaromatic carbon atoms per repeating unit to be present in the substituents. Preference is here given to at least 4 carbon atoms, particularly preferably at least 8 carbon atoms. Some of these carbon atoms may also be replaced by O or S. However, it is also possible for a particular proportion of repeating units, either units of the formula (I) or (II) or of other structural types, to bear no further nonaromatic substituents.

In order to prevent the morphology of the film from being adversely affected, preference is given to there being no long-chain substituents having more than 12 carbon atoms in a linear chain, preferably no substituents having more than 8 carbon atoms, particularly preferably no substituents having more than 6 carbon atoms.

Nonaromatic carbon atoms are, as in the description of, for example, $R^1$, present in appropriate straight-chain, branched or cyclic alkyl or alkoxy chains.

Preference is given to polymers according to the invention in which X=C—H or C—$R^1$. Preference is also given to polymers according to the invention in which the symbol Z represents a single chemical bond.

Furthermore, preference is given to polymers according to the invention in which:

$R^1$ is identical or different on each occurrence and is a straight-chain, branched or cyclic alkyl or alkoxy chain which has from 1 to 10 carbon atoms and in which one or more H atoms may also be replaced by fluorine, or an aryl group which has from 6 to 14 carbon atoms and which is also substituted by one or more nonaromatic radicals $R^1$.

Furthermore, particular preference is given to polymers according to the invention in which:

$R^1$ is identical or different on each occurrence and is a straight-chain or branched alkyl or alkoxy chain having from 1 to 8 carbon atoms or an aryl group which has from 6 to 10 carbon atoms and is also substituted by one or more nonaromatic radicals $R^1$;

n are identical or different and are each 1 or 2.

Furthermore, preference is given to polymers according to the invention in which:

$R^2$ is identical or different on each occurrence and is a straight-chain or branched alkyl or alkoxy chain which has from 1 to 10 carbon atoms and in which one or more H atoms may also be replaced by fluorine, an aryl or aryloxy group which has from 6 to 14 carbon atoms and which may also be substituted by one or more nonaromatic radicals $R^1$, or CN;

o, m are identical or different on each occurrence and are each 0 or 1.

Furthermore, particular preference is given to polymers according to the invention in which:

$R^2$ is identical or different on each occurrence and is a straight-chain or branched alkyl or alkoxy chain which has from 1 to 8 carbon atoms and in which one or more H atoms may also be replaced by fluorine, or an aryl group which has from 6 to 10 carbon atoms and which may also be substituted by one or more nonaromatic radicals $R^1$;

o, m are identical or different on each occurrence and are each 0 or 1, with o and m being 0 for at least 50%, preferably at least 70%, very particularly preferably at least 90%, of all repeating units of the formulae (I) and (II) present in the polymer.

Furthermore, preference is given to polymers according to the invention in which:

$R^3$, $R^4$ are identical or different on each occurrence and are each a straight-chain, branched or cyclic alkyl chain which has from 1 to 10 carbon atoms and in which one or more nonadjacent carbon atoms may also be replaced by O, where one or more H atoms may also be replaced by fluorine, or an aryl group which has from 5 to 40 carbon atoms and in which one or more carbon atoms may also be replaced by O, S or N and which may also be substituted by one or more nonaromatic radicals $R^1$.

Particular preference is given to polymers according to the invention in which:

$R^3$, $R^4$ are identical or different on each occurrence and are each an aryl group which has from 6 to 14 carbon atoms and may also be substituted by one or more nonaromatic radicals $R^1$.

Very particular preference is given to polymers according to the invention in which:

$R^3$, $R^4$ are identical or different on each occurrence and are each an aryl group which has from 6 to 14 carbon atoms and which may also be substituted by one or more nonaromatic radicals $R^1$ and in which the substituents $R^3$ and $R^4$ are different from one another on a unit of the formula (II). Substituents which have identical aryl groups but bear different radicals $R^1$ or have these in different positions are regarded as being different for the present purposes.

This latter preference in particular leads to a tremendous improvement in the solubility properties without the morphological properties being adversely affected at the same time.

The polymers of the invention are per se copolymers which have at least two different repeating units (formula (I) and formula (II)). Furthermore, preference is also given to copolymers which have further, different repeating units which have structures different from those of the formulae (I) and (II). Such further structures are described in more detail below. The copolymers of the invention can have random, alternating or block structures, or have an alternating sequence of a plurality of these structures.

However, preference is also given to copolymers according to the invention which comprise one or more different structures of the formula (I) and one or more different structures of the formula (II).

The use of a plurality of different structural elements enables properties such as solubility, solid phase morphology, color, etc., to be adjusted.

Preferred copolymers which contain further structural elements in addition to those of the formula (I) and the formula (II) are ones in which at least one further structural element has charge transport properties.

For the purposes of the present patent application, the following applies to such structural elements: if HOMOPOLYMERS or HOMOOLIGOMERS are to be produced from these structural elements, these have, at least in the case of one charge carrier, i.e. either electrons or holes, a higher charge carrier mobility than is the case in a polymer according to the invention which consists exclusively of structural elements of the formula (I) and the formula (II). The charge carrier mobility (measured in $cm^2/(V*s)$) is preferably greater by a factor of at least 10, particularly preferably at least 50.

Structural elements which have hole transport properties are, for example, triarylamine derivatives, benzidine derivatives, tetraarylene-para-phenylenediamine derivatives, phenothiazine derivatives, phenoxazine derivatives, dihydrophenazine derivatives, thianthrene derivatives, benzo-p-dioxin derivatives, phenoxathiine derivatives, carbazole derivatives, azulene derivatives, thiophene derivatives, pyrrole derivatives, furan derivatives and further O-, S- or N-containing heterocycles having a high HOMO (HOMO=highest occupied molecular orbital); these heterocycles preferably have a HOMO at less than 6.0 eV (relative to vacuum level), particularly preferably less than 5.5 eV.

Preference is for this purpose given to polymers according to the invention which further comprise at least one structural unit of the formulae (III) to (XIX). The proportion of these structural elements is at least 1%, preferably at least 5%. The maximum proportion is not more than 70%, preferably not more than 50%. These structural units, too, can be incorporated in the polymer in a random, alternating or block fashion.

Formula (III)

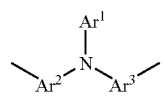

Formula (IV)

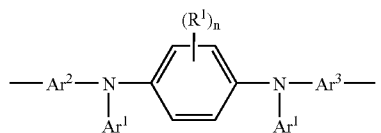

Formula (V)

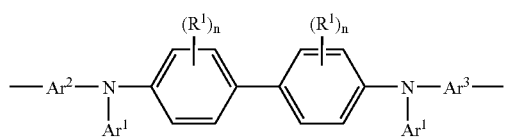

Formula (VI)

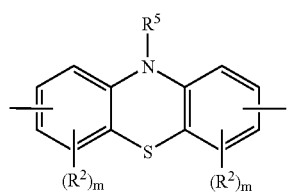

Formula (VII)

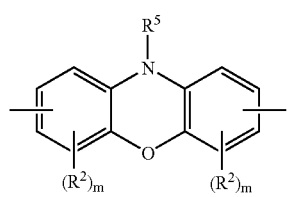

Formula (VIII)

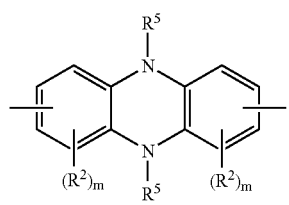

Formula (IX)

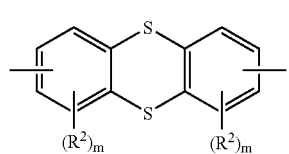

Formula (X)

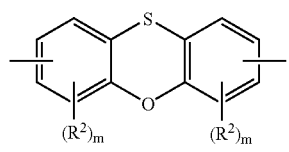

Formula (XI)

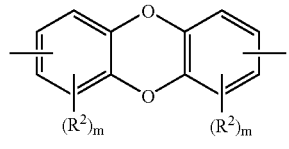

Formula (XII)

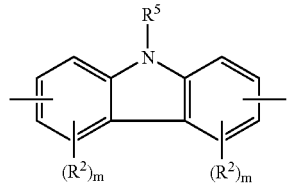

Formula (XIII)

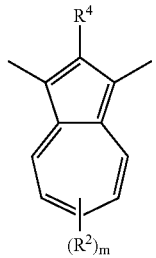

Formula (XIV)

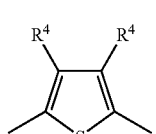

Formula (XV)

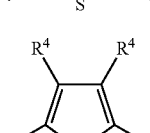

Formula (XVI)

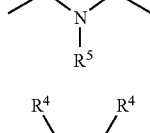

Formula (XVII)

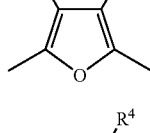

Formula (XVIII)

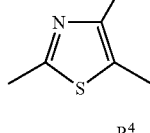

Formula (XIX)

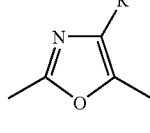

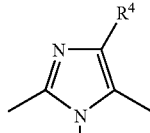

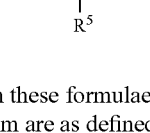

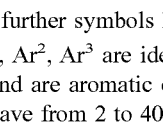

In these formulae, the symbols $R^1$ to $R^5$ and the indices n and m are as defined under formula (I) and formula (II), and the further symbols have the following meanings:

$Ar^1$, $Ar^2$, $Ar^3$ are identical or different on each occurrence and are aromatic or heteroaromatic hydrocarbons which have from 2 to 40 carbon atoms and may also be substituted by one or more nonaromatic radicals $R^1$.

$Ar^1$, $Ar^2$, $Ar^3$ are preferably substituted or unsubstituted aromatic hydrocarbons having from 6 to 20 carbon atoms, particularly preferably appropriate benzene, naphthalene, anthracene, pyrene or perylene derivatives.

The way in which these structures are incorporated is determined directly in the case of many (cf., for example, formulae (III) to (V) and formulae (XIII) to (XIX)). In the case of other structures, a plurality of possibilities exist in each case according to the invention. However, these also have preferred modes of incorporation:

In the case of the N-containing tricyclic heterocycles (formula (VI) to formula (VIII)), linkage via carbon atoms in the para position relative to the nitrogen (i.e. in the case of phenothiazine and phenoxazine derivatives: 3,7 positions; in the case of dihydrophenazine derivatives: 2,7 or 3,7 positions) is preferred in each case. An analogous situation applies to carbazole derivatives (formula (XII)). On the other hand, both ortho and para positions relative to one of the heteroatoms are preferred in the case of the O- and/or S-containing tricycles (formulae (IX) to (XI))

Monomers for the incorporation of structural units of formula (III), formula (IV) and formula (V) can be synthesized as described in, for example, WO98/06773. Monomers for the incorporation of structural units of formula (VI), formula (VII) and formula (VIII) can be synthesized as described in, for example, M. Jovanovic et al., *J. Org. Chem.* 1984, 49, 1905, and H. J. Shine et al., *J. Org. Chem.* 1979, 44, 3310. Monomers for the incorporation of structural units of formula (IX) and formula (X) can be synthesized as described in, for example, J. Lovell et al., *Tetrahedron* 1996, 52, 4745, U.S. Pat. No. 4,505,841 and the references cited therein.

Monomers for the incorporation of structural units of the formula (XI) can be synthesized as described in, for example, A. D. Kuntsevich et al., *Zh. Obshch. Khim.* 1994, 64,1722, and A. D. Kuntsevich et al., *Dokl. Akad. Nauk* 1993, 332,461. A wide variety of halogenated monomers for the incorporation of structural units of the formula (XII) are known from the literature and some of them are even commercially available. A listing of all possible methods would be superfluous in the present patent application.

Monomers for the incorporation of structural units of the formula (XIII) can be synthesized as described in, for example, R. H. Mitchell et al., *Org. Prep. Proced. Int.* 1997, 29, 715.

A wide variety of halogenated monomers for the incorporation of structural units of the formula (XIV) are known from the literature and some of these are even commercially available. A listing of all possible methods would be superfluous in the present patent application.

Monomers for the incorporation of structural units of the formula (XV) can be synthesized as described in, for example, H. M. Gilow et al., *J. Org. Chem.* 1981, 46, 2221 and G. A. Cordell, *J. Org. Chem.* 1975, 40, 3161.

Monomers for the incorporation of structural units of the formula (XVI) can be synthesized as described in, for example, M. A. Keegstra et al., *Synth. Commun.* 1990, 20, 3371 and R. Sornay et al., *Bull. Soc. Chim. Fr.* 1971, 3, 990, and some of them are also commercially available.

Some monomers suitable for the incorporation of structural units of the formula (XVII) are commercially available.

Monomers for the incorporation of structural units of the formula (XVIII) can be synthesized as described in, for example, JP 63-250385.

Monomers for the incorporation of structural units of the formula (XIX) can be synthesized as described in, for example, M. El Borai et al., *Pol. J. Chem.* 1981, 55, 1659, and some of them are also commercially available.

The literature references cited here for the synthesis of monomers which produce structures of the formulae (III) to (XIX) in the polymer describe mainly the synthesis of halogen derivatives, preferably bromine derivatives. A person skilled in the art can readily prepare, for example, boronic acid derivatives or stannates from them. This can be achieved, for example, by metallation (e.g. with Mg (Grignard reaction) or Li (e.g. by means of BuLi)) and subsequent reaction with appropriate boron or tin derivatives, e.g. trialkyl borates or trialkyltin halides. However, it is naturally also possible to produce boronic acid derivatives from the corresponding bromides by reaction with diboranes in the presence of transition metal catalysts. Many further methods are known from the literature and can naturally also be used by a person skilled in the art.

Structural elements having electron transport properties are, for example, pyridine derivatives, pyrimidine derivatives, pyridazine derivatives, pyrazine derivatives, oxadiazole derivatives, quinoline derivatives, quinoxaline derivatives, phenazine derivatives and further O-, S- or N-containing heterocycles having a low LUMO (LUMO=lowest unoccupied molecular orbital); these heterocycles preferably have a LUMO of more than 2.7 eV (relative to vacuum level), particularly preferably more than 3.0 eV.

Preference is here given to polymers according to the invention which further comprise at least one structural unit of the formulae (XX) to (XXX). The proportion of these structural elements is at least 1%, preferably at least 5%. The maximum proportion is not more than 70%, preferably not more than 50%. These structural units, too, can be incorporated in the polymer in a random, alternating or block fashion.

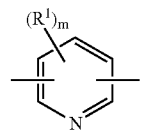

Formula (XX)

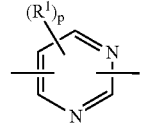

Formula (XXI)

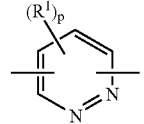

Formula (XXII)

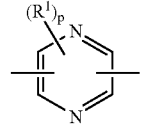

(XXIII)

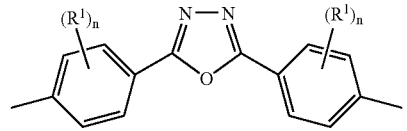

(XXIV)

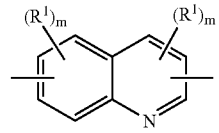

(XXV)

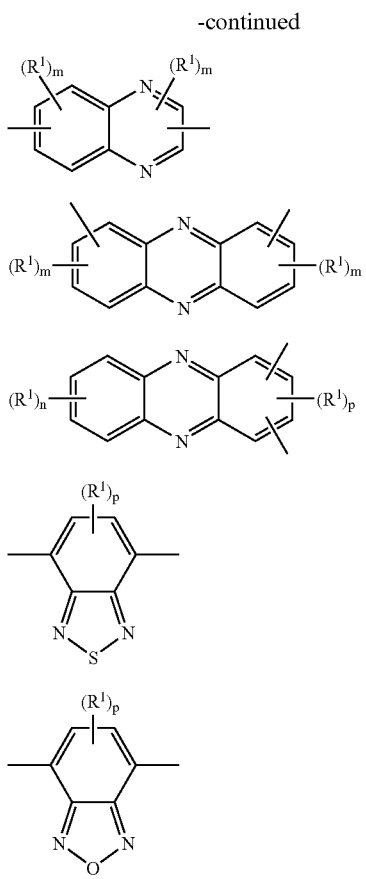

Formula (XXVI)

Formula (XXVII)

Formula (XXVIII)

Formula (XXIX)

Formula (XXX)

In these formulae, the symbol $R^1$ and the indices n and m are as defined under formula (I) and formula (II), and the index p is 0, 1 or 2, preferably 0 or 1.

The way in which these structures are incorporated is determined directly in the case of many (cf., for example, formulae (XXIV), (XXIX) and (XXX)). In the case of other structures, a plurality of possibilities exists in each case according to the invention. However, there are also preferred modes of incorporation for these:

In the case of pyridine derivatives, linkage via the 2,5 or 2,6 positions is preferred; in the case of pyrazine and pyrimidine derivatives, linkage via the 2,5 positions is preferred and in the case of pyridazine derivatives linkage via the 3,6 positions is preferred.

In the case of the bicyclic heterocycles, a number of linkages are generally possible and also preferred. However, in the case of quinoxaline, clear preference is given to linkage via the 5,8 positions.

In the case of phenazine, it can, as indicated, be preferred either that linkage occurs via the two outer rings or that incorporation occurs on only one ring. Preferred positions are thus incorporation at carbon atoms 1,4 or 2,3 or 2,7 or 3,7.

The chemistry of pyridine derivatives (XX) has been studied very extensively. Thus, the preparation of 2,5- and 2,6-dihalopyridines is likewise known. Reference may hereby be made to the numerous standard works on heterocyclic chemistry. Furthermore, many of the compounds are also commercially available. Monomers for the incorporation of structural units of the formula (XXI) can be synthesized as described in, for example, Arantz et al., *J. Chem. Soc. C* 1971,1889. Monomers for the incorporation of structural units of the formula (XXII) can be synthesized as described in, for example, Pedrali et al., *J. Org. Synth*. 1958, 23, 778.

Monomers for the incorporation of structural units of the formula (XXIII) can be synthesized as described in, for example, Ellingson et al., *J. Am. Chem. Soc*. 1949, 71, 2798.

Monomers for the incorporation of structural units of the formula (XXIV) can be synthesized as described in, for example, Stolle et al., *J. Prakt. Chem*. 1904, 69, 480.

Monomers for the incorporation of structural units of the formula (XXV) can be synthesized as described in, for example, Metzger, Chem. Ber. 1884, 17, 187, and A. I. Tochilkin et al., *Chem. Heterocycl. Compd. (Engl. Transl)* 1988, 892.

Monomers for the incorporation of structural units of the formula (XXVI) can be synthesized as described in, for example, Calhane et al., *J. Am. Chem. Soc*. 1899, 22, 457, and T. Yamamoto et al., *J. Am. Chem. Soc*. 1996, 118, 3930.

Monomers for the incorporation of structural units of the formulae (XXVII) and (XXVIII) can be synthesized as described in, for example, L. Horner et al., *J. Liebigs Ann. Chem*., 1955, 597, 1, and P. R. Buckland et al., *J. Chem. Res. Miniprint* 1981, 12, 4201.

Monomers for the incorporation of structural units of the formula (XXIX) can be synthesized as described in, for example, K. Pilgram et al., *J. Heterocyc. Chem*. 1970, 7, 629, and WO 00/55927.

Monomers for the incorporation of structural units of the formula (XXX) can be synthesized as described in, for example, Hammick et al., *J. Chem. Soc*. 1931, 3308, and K. Pilgram et al., *J. Heterocycl. Chem*. 1974, 11, 813.

The references cited here for the synthesis of monomers which form structures of the formulae (XX) to (XXX) in the polymer also describe mainly the synthesis of halogen derivatives, preferably bromine derivatives. A person skilled in the art can, as also described above in the case of the units which increase hole mobility, carry out further transformations of these, e.g. to produce boronic acid derivatives or stannates.

Furthermore, preference is also given to polymers according to the invention in which both units which increase the hole mobility and units which increase the electron mobility are present.

Particular preference is accordingly given to polymers according to the invention which comprise one or more structures of the formulae (III) to (XIX) together with one or more structures of the formulae (XX) to (XXX).

The abovementioned limits to the respective proportions continue to apply here. It can be very particularly preferred for the polymers of the invention to comprise units in which structures which increase hole mobility and structures which increase electron mobility are present in direct succession or alternate, as is the case in, for example, the formulae (XXXI) to (XXXXV):

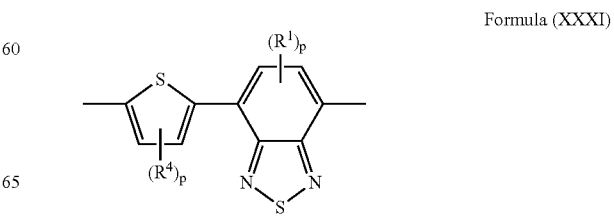

Formula (XXXI)

Formula (XXXII)
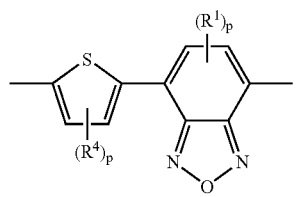
Formula (XXXIII)
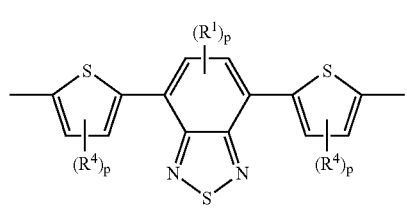
Formula (XXXIV)
Formula (XXXV)
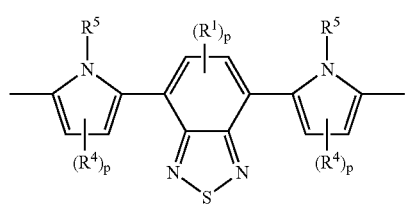
Formula (XXXVI)
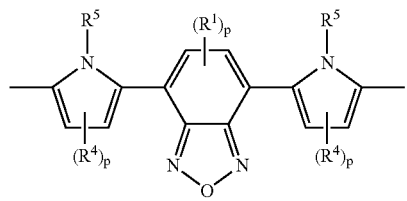
Formula (XXXVII)
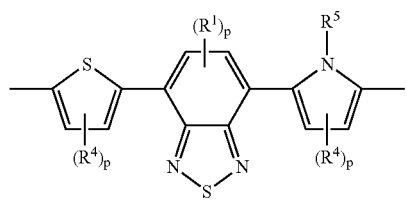
Formula (XXXVIII)
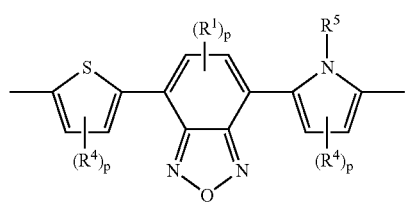
Formula (XXXIX)
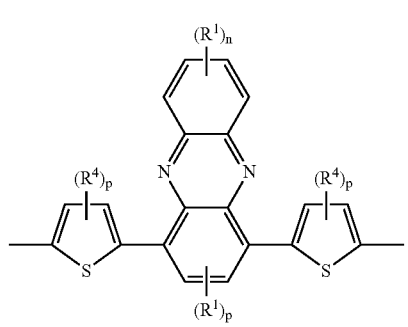
Formula (XXXX)
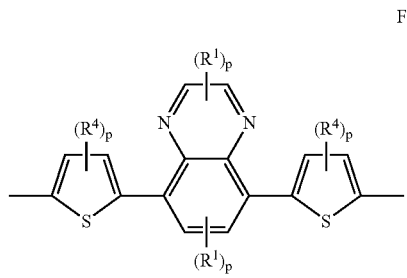
Formula (XXXXI)
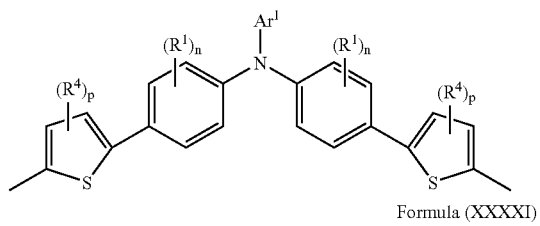
Formula (XXXXII)
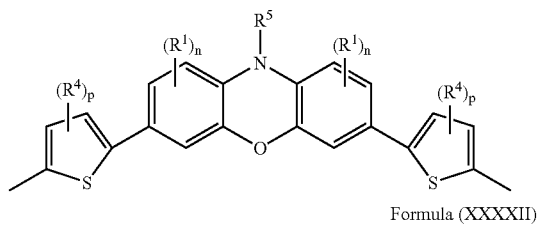
Formula (XXXXIII)
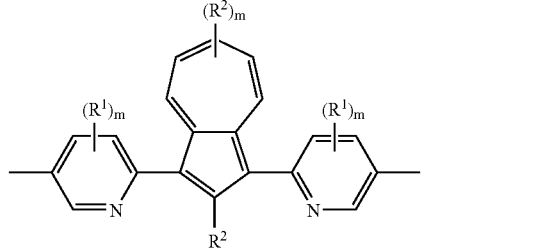
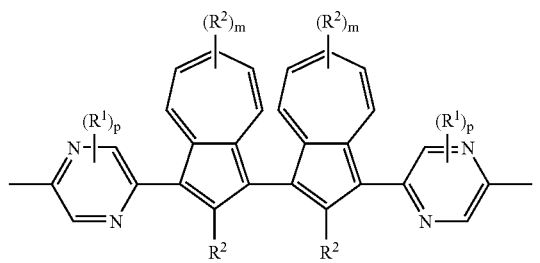

Formula (XXXXIV)

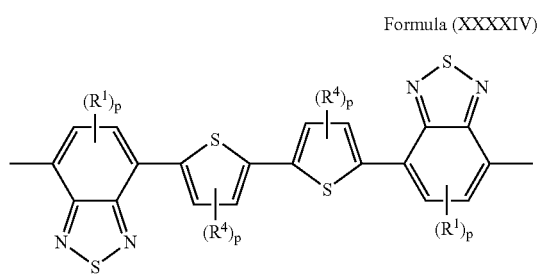

Formula (XXXXV)

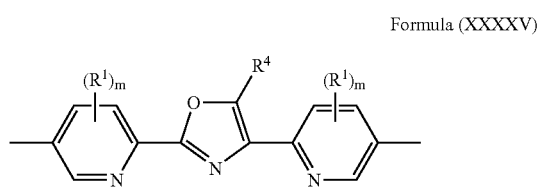

Monomers of the formulae (XXXI) to (XXXXV) can be synthesized using the methods indicated for the formulae (III) to (XXX) by appropriate combination of the appropriate precursors. Attention may be drawn to the fact that at least some examples of these syntheses are described in the abovementioned patent applications WO 00/46321 and WO 00/55927. Furthermore, structures of this type are also reported in, for example, H. A. M. Mullekom et al., *Chem. Eur. J.*, 1998, 4, 1235. It may also be pointed out that the structures of the formulae (XXXI) to (XXXXV) are in no way intended to restrict the scope of the invention, and a person skilled in the art can naturally easily synthesize appropriate combinations of the abovementioned structures (III) to (XIX) and (XX) to (XXX) and incorporate these into the polymers of the invention.

Preferred copolymers which further comprise additional structural elements in addition to those of formula (I) and formula (II) also include ones which contain at least one additional aromatic or other conjugated structure which does not come under the abovementioned groups, i.e. has no influence or only little influence on the charge carrier mobilities. Such structural elements can influence the morphology and also, in particular, the emission color of the resulting polymers.

Preference is given to aromatic structures which have from 6 to 40 carbon atoms or stilbene or bisstyrylarylene derivatives which may each be substituted by one or more nonaromatic radicals $R^1$.

Particular preference is given to the incorporation of 1,4-phenylene, 1,4-naphthylene, 1,4- or 9,10-anthracenylene, 1,6- or 2,7- or 4,9-pyrene, 3,9- or 3,10-perylene, 2,7- or 3,6-phenanthrene, 4,4'-biphenylene, 4,4"-terphenylene, 4,4'-bi-1,1'-naphthylene, 4,4'-stilbene or 4,4"-bisstyrylarylene derivatives.

Many structures of this type are known in the literature and most of them are also commercially available. A listing of all possible variants of the synthesis would be superfluous in the present patent application.

Preferred copolymers which further comprise additional structural elements in addition to those of formula (I) and formula (II) also include ones in which organometallic complexes are incorporated into the main chain. Particular preference is in this case given to complexes of the d transition metals, very particularly preferably complexes of the higher metals of the iron, cobalt and nickel triads, i.e. complexes of ruthenium, osmium, rhodium, iridium, palladium and platinum. Such complexes are frequently able to emit light from excited triplet states, which frequently increases the energy efficiency. The use of such complexes in low molecular weight OLEDs is described, for example, in M. A. Baldo, S. Lamansky, P. E. Burrows, M. E. Thompson, S. R. Forrest, Applied Physics Letters, 1999, 75, 4-6. Nothing has been reported hitherto about the incorporation of these compounds in polymers. Appropriate monomers are described in the not yet published patent application DE 10109027.7. Such structural elements can also exert an influence on the morphology and in particular on the emission color and the energy efficiency of the resulting polymers.

Examples of particularly preferred complexes which can be incorporated into the polymers of the invention are the compounds of the formulae (XXXXVI) to (XXXXIX).

Formula (XXXXVI)

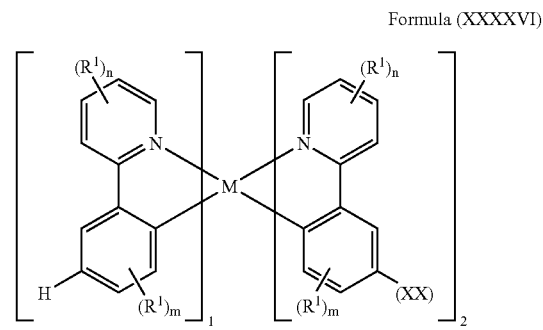

Formula (XXXXVII)

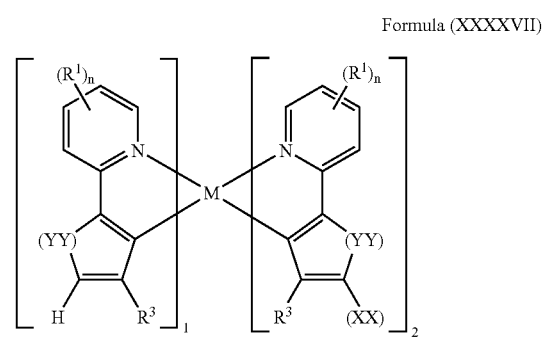

Formula (XXXXVIII)

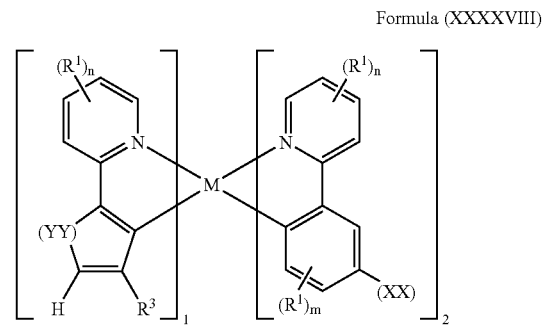

-continued

Formula (XXXXIX)

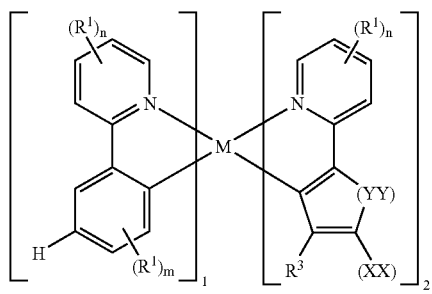

In these formulae, the symbols $R^1$ and $R^3$ and the indices n and m are as defined under the formulae (I) and (II); and M is Rh or Ir XX corresponds to the linkage point in the polymer YY is identical or different on each occurrence and is O, S or Se.

The preparation of such monomers is described in the abovementioned unpublished patent application DE 10109027.7 which is hereby incorporated by reference into the disclosure of the present invention.

The polymers of the invention are then generally prepared by polymerization of two or more monomers of which at least one subsequently forms structures of the formula (I) and at least one further monomer forms structures of the formula (II). There are in principle a relatively large number of different polymerization reactions suitable for this purpose, but the types described below have been found to be particularly useful. In principle, all these types of reaction form C—C linkages:

(A) Polymerization by the SUZUKI method: here, dihalides and bisboronic acids or appropriate derivatives, or corresponding monohalide-monoboronic acid derivatives, are used as monomers and are coupled in the presence of palladium catalysts and solvents under basic conditions. Reactions of this type leading to conjugated polymers have been described many times. There has been a whole series of proposals for making such reactions proceed efficiently and give high molecular weight polymers; these are, inter alia, described in the following references: (i) EP 707.020, (ii) EP 842.208, (iii) EP 1.025.142, (iv) WO 00/53656, and (v) the references cited therein. The corresponding descriptions are hereby incorporated by reference into the disclosure of the present patent application.

(B) Polymerizations by the YAMAMOTO method: here, only dihalides are used as monomers. These are carried out in the presence of solvents, a nickel compound, a base and, if desired, a reducing agent and further ligands. Reactions of this type leading to conjugated polymers have been described a number of times in the past. There are some proposals for making such reactions proceed efficiently and give high molecular weight polymers; these are described, inter alia, in the following references: (i) M. Ueda et al., Macromolecules, 1991, 24, 2694, (ii) T. Yamamoto et al., Macromolecules 1992, 25, 1214, (iii) T. Yamamoto et al., Synth. Met. 1995, 69, 529-31, (iv) T. Yamamoto et al., J. Organometallic Chem. 1992, 428, 223, (v) I. Colon et al., J. Poly. Sci.: Part A: Poly. Chem. 1990, 28, 367, (vi) T. Yamamoto et al., Macromol. Chem. Phys. 1997, 198, 341. The corresponding descriptions are hereby incorporated by reference into the disclosure of the present patent application.

(C) Polymerizations by the STILLE method: here, dihalides and bisstannates, or corresponding monohalide-monostannates, are used as monomers and are coupled in the presence of palladium catalysts and solvents under basic conditions. Reactions of this type leading to conjugated polymers have been described. However, there is not as broad a range of developments in this case as for the SUZUKI or YAMAMOTO coupling. One conjugated polymer obtained by STILLE coupling is described, for example, in W. Schorf et al., J. Opt. Soc. Am. B 1998, 15, 889. A review of the possibilities and difficulties of the STILLE reaction is given, inter alia, by V. Farina, V. Krishnamurthy, W. J. Scott (editors) "The Stille Reaction" 1998, Verlag: Wiley, New York, N.Y. The corresponding descriptions are hereby incorporated by reference into the disclosure of the present patent application.

After the polymerization (polycondensation) has been carried out, the polymers synthesized firstly have to be separated from the reaction medium. This is generally achieved by precipitation in a nonsolvent. The polymers obtained subsequently have to be purified, since the content of low molecular weight organic impurities and also the ion content or content of other inorganic impurities sometimes have very great effects on the use properties of the polymers in PLEDs. Thus, low molecular weight constituents can considerably reduce the efficiency and also dramatically worsen the operating life. The presence of inorganic impurities has analogous effects. Suitable purification methods include precipitation processes in which the polymer is dissolved and precipitated in a nonsolvent a number of times. In such a case, it is useful to pass the polymer solution through a filter to remove undissolved constituents (crosslinked gel particles) and also dust particles. A further possibility is the use of ion exchangers to reduce the ion content. Here, stirring a polymer solution with an aqueous solution containing, for example, chelating ligands can also help. Further organic or inorganic extraction processes, e.g. using solvent/nonsolvent mixtures or using supercritical $CO_2$, can also give considerable improvements in this case.

The novel polymers obtained in this way can then be used in PLEDs. This is in general carried out using the following general method which is then naturally adapted appropriately to the individual case:

A substrate (e.g. glass or a plastic such as specifically treated PET) is coated with a transparent anode material (for example indium-tin oxide, ITO); the anode is subsequently structured and connected in a manner appropriate to the desired application (e.g. by photolithography). It is possible in this case for the entire substrate and the appropriate circuitry firstly to be produced by a quite complicated process so as to make active matrix drive possible.

A conductive polymer, e.g. a doped polythiophene or polyaniline derivative, is then generally applied either over the entire area or only to the active (=anodic) places. This is generally carried out by means of coating processes which apply a dispersion of the corresponding polymer. The processes described below for the light-emitting polymer are in principle suitable for this purpose. The thickness of this polymer layer can vary within a wide range, but for practical applications will be in the range from 10 to 1000 nm, preferably from 20 to 500 nm.

Depending on the application, a solution of a polymer according to the invention is then applied. For polychrome or full color display elements, a plurality of different solutions are then applied in various regions to produce appropriate colors.

For this purpose, the polymers according to the invention are firstly dissolved individually (it may also be advisable to use blends of two or more polymers) in a solvent or solvent mixture and then filtered. Since the organic polymers and, especially, the interfaces in the PLED are sometimes extremely sensitive to oxygen or other components of the air, it is advisable to carry out this operation under protective gas. Suitable solvents are aromatic liquids such as toluene, xylenes, anisole, chlorobenzene or else other solvents such as cyclic ethers (e.g. dioxane, methyldioxane) or amides, for example NMP or DMF, or solvent mixtures as are described in the unpublished patent application DE 10111633.0. The previously coated supports can then be coated with these solutions, either over their entire area, e.g. by spin coating methods or doctor blade techniques, or else in a resolved manner by printing methods such as inkjet printing, offset printing, screen printing, gravure printing and the like.

If desired, electron injection materials can then be applied to these polymer layers, e.g. by vapor deposition or from solution, using methods as have been described for the emitting polymers. Electron injection materials used can be, for example, low molecular weight compounds such as triarylborane compounds or aluminum trishydroxyquinolinate ($Alq_3$) or appropriate polymers such as polypyridine derivatives and the like. It is also possible to convert thin layers of the emitting polymer into electron injection layers by appropriate doping.

A cathode is subsequently applied by vapor deposition. This is generally carried out by means of a vacuum process and can occur, for example, either by thermal vapor deposition or by plasma spraying (sputtering). The cathode can be applied over the entire area or in structured form with the aid of a mask. Metals having a low work function, e.g. alkali metals, alkaline earth metals and f transition metals, e.g. Ca, Mg, Sr, Ba, Yb, Sm or aluminum, or alloys of metals or else multilayer structures comprising various metals are generally used as cathode. In the case of multilayer structures, it is also possible to make concomitant use of metals which have a relatively high work function, e.g. Ag. It can also be preferred for a very thin dielectric layer (e.g. LiF or the like) to be inserted between the metal and the emitting polymer or the electron injection layer. The cathodes generally have a thickness of from 10 to 10000 nm, preferably from 20 to 1000 nm.

The PLEDs or displays produced in this way are subsequently connected and encapsulated appropriately and then tested or used.

As described above, the polymers of the invention are particularly useful as electroluminescence materials in the PLEDs or displays produced in this way.

For the purposes of the invention, electroluminescence materials are materials which can be used as active layer in a PLED. The term "active layer" means that the layer is capable of emitting light on application of an electric field (light-emitting layer) and/or that it improves the injection and/or transport of the positive and/or negative charges (charge injection layer or charge transport layer).

The invention therefore also provides for the use of a polymer according to the invention in a PLED, in particular as electroluminescence material.

The invention thus likewise provides a PLED having one or more active layers in which at least one of these active layers comprises one or more polymers according to the invention. The active layer can be, for example, a light-emitting layer and/or a transport layer and/or a charge injection layer.

PLEDs are used, for example, as self-illuminating display elements, e.g. indicator lamps, alphanumeric displays, polychrome or full color displays, signs, and in optoelectronic couplers.

In the present patent application and in the following examples, the use of polymers according to the invention or blends of polymers according to the invention in PLEDs and the corresponding displays is specifically addressed. Despite this restriction of the description, a person skilled in the art can, without making a further inventive step, also utilize the polymers of the invention in other electronic devices for further applications, e.g. for organic integrated circuits (O-ICs), in organic field effect transistors (OFETs), in organic thin film transistors (OTFTs), for organic solar cells (O-SCs) or in organic laser diodes (O lasers), to name only a few applications. The invention is illustrated by the following examples without being restricted thereby.

Part A: Synthesis of the Monomers:

A1: Monomers for Units of the Formula (I) (Spiro Compounds)

EXAMPLE M1/M2

Preparation of 2,7-dibromo-2',3',6',7'-tetra(2-methylbutyloxy)spirobifluorene and the ethylene glycol ester of 2',3',6',7'-tetra(2-methylbutyloxy)spirobifluorene-2,7-bisboronic acid Preparation of 3,3',4,4'-tetra(2-methylbutyloxy)biphenyl 229.405 g (696.6 mmol) of 3,4-bis(2-methylbutyloxy)-1-bromobenzene, 215 g (731 mmol) of 3,4-bis(2-methylbutyloxy)benzeneboronic acid and 202.1 g (1.462 mol) of $K_2CO_3$ were suspended in 800 ml of toluene and 800 ml of water and the mixture was saturated with $N_2$ for 1 hour. 1.74 g (1.505 mmol) of $Pd(PPh_3)_4$ was subsequently added under protective gas. The turbid, slightly yellowish mixture was stirred vigorously under reflux for about 7 hours under nitrogen. After cooling, the organic phase was stirred with 500 ml of 1% strength NaCN solution. The phases were separated and the organic phase was washed with water, dried over $Na_2SO_4$ and evaporated on a rotary evaporator. This gave 339 g (679.7 mmol, 98%) of a light-brown oil which, according to $^1H$ NMR, had a purity of 97% and was used directly in the subsequent reaction.

$^1H$ NMR ($CDCl_3$, 500 MHz): 7.05 (s, 2H, H2/H2'); 7.04 (d, 2H, H6/H6', J=8.5); 6.91 (d, 2H, H5/H5', J=8.6); 3.94-3.77 (m, 8H, $OCH_2$); 1.98-1.82 (m, 4H, H—C); 1.68-1.58 (m, 4H, $CH_2$); 1.39-1.25 (m, 4H, $CH_2$); 1.07-0.93 (m, 24 H, $8 \times CH_3$).

Preparation of 2-bromo-4, 5,3'4'-tetra(2-methylbutyloxy)biphenyl 339 g (679.7) mmol of 3,3',4,4'-tetra(2-methylbutyloxy) biphenyl were dissolved in 800 ml of ethyl acetate. 120.98 g (679.7 mmol) of N-bromosuccinimide were then added in solid form over a period of 15 minutes under protective gas, in the absence of light and with cooling to 0-5° C. The suspension was slowly warmed to room temperature under a blanket of protective gas and was then stirred vigorously at room temperature for 4 hours. 500 ml of ethyl acetate and 300 ml of water were added, the phases were separated and the aqueous phase was extracted twice with 100 ml each time of ethyl acetate. The combined organic phases were washed twice with 50 ml each time of water and dried over $MgSO_4$. The oil obtained was filtered through silica gel with the aid of hexane. Taking off the solvent gave 361.2 g (625.3 mmol, 92%) of 2-bromo-4,5,3',4'-tetra(2-methylbutyloxy) biphenyl as a colorless oil.

$^1$H NMR ($CDCl_3$, 500 MHz): 7.10 (s, 1H, H6); 6.93 (d, 1H, H6', J=1.3 Hz); 6.88 (s, 1H, H3); 6.87 (d, 1H, H5', J=1.4 Hz); 6.38 (s, 1H, H2'); 3.92-3.73 (m, 8H, $OCH_2$); 1.98-1.84 (m, 4H, H—C); 1.68-1.54 (m, 4H, $CH_2$); 1.37-1.25 (m, 4H, $CH_2$); 1.08-0.91 (m, 24 H, 8×$CH_3$).

Preparation of 2,7-dibromo-2',63'7'-tetra(2-methylbutyloxy) spirobifluorene (M1)

360 g (623.2 mmol) of 2-bromo-4,5,3',4'-tetra(2-methylbutyloxy)biphenyl were dissolved in 400 ml of distilled THF. 15.59 g (641.89 mmol, 1.03 eq) of magnesium turnings and a few crystals of iodine were placed in a reaction vessel under $N_2$.

These were heated briefly and 10% of the amount of starting material in THF were added. After the reaction had started, the remainder was added at such a rate that the reaction mixture refluxed on its own without further heating (one hour). The mixture was refluxed for a further 2 hours and a further 100 ml of distilled THF were then added.

A suspension of 210.64 g (623.2 mmol) of 2,7-dibromofluoren-9-one in 800 ml of distilled THF was cooled to 0° C. The Grignard solution was then added dropwise to the suspension at a temperature of 0-5° C. The mixture was subsequently refluxed for 90 minutes.

After cooling to room temperature, a mixture of 755 ml of ice water and 41.7 ml of HCl (37% strength) was added to the reaction mixture and the entire mixture was stirred for 30 minutes. The organic phase was firstly washed with $NaHCO_3$ solution (2×30 ml) and then with water (2×100 ml), dried over sodium sulfate and evaporated on a rotary evaporator. This gave 530 g of a light-brown oil which was immediately reacted further.

The oil was admixed with 1250 ml of acetic acid and 18.5 ml of concentrated hydrochloric acid and heated to boiling under nitrogen. After 10 minutes, 200 ml of acetic acid were added. After 2 hours, the mixture was cooled to room temperature, the solid which had precipitated was filtered off and washed firstly with 200 ml of acetic acid and then with 200 ml of water and dried under reduced pressure. The solid was stirred with methanol and dried overnight at 40° C. in a drying oven.

The solid was recrystallized twice from 2-butanone. This gave 329.7 g (402.7 mmol, 64%) of 2,7-dibromo-2',3',6',7'-tetra(2-methylbutyloxy)spirobifluorene as a colorless solid which, according to HPLC (Zorbax SB-C18 3.5 μm, 4.6×75 mm, 90% methanol/10% THF, 1 ml/min, UV detection 230-330 nm), had a purity of >99.8%.

$^1$H NMR ($CDCl_3$, 400 MHz): 7.64 (d, 2 H, H4/5, J=8.0 Hz); 7.47 (dd, 2 H, H3/6, J=8.0, 1.9 Hz); 7.19 (d, 2H, H1'/8', J~1.5 Hz); 6.85 (s, 2H, H4'/5'); 6.12 (s, 2H, H1'/8'); 3.97-3.83 (m, 4H, 2×$OCH_2$); 3.58-3.45 (m, 4H, 2×$OCH_2$); 2.02-1.89 (m, 2H, H—C); 1.80-1.70 (m, 2H, H—C); 1.68-1.59 (m, 2H, $CH_2$); 1.53-1.42 (m, 2H, $CH_2$); 1.39-1.26 (m, 2H, $CH_2$); 1.22-1.10 (m, 2H, $CH_2$); 1.08 (d, 6H, 2×$CH_3$, J=6.7 Hz); 0.95 ((φt, 6H, 2×$CH_3$, J=7.4 Hz); 0.93 (d, 6H, 2×$CH_3$, J=6.9 Hz); 0.86 ((pt, 6H, 2×$CH_3$, J=7.4 Hz).

Preparation of the ethylene glycol ester of 2',3',6',7'-tetra(2-methylbutyloxy)spirobifluorene-2,7-bisboronic acid (M2)

150 g (183 mmol) of 2,7-dibromo-2',3',6',7'-tetra(2-methylbutyloxy)spirobifluorene were dissolved in 500 ml of distilled THF. 11.2 g (458 mmol) of magnesium turnings were admixed under argon with a little iodine, heated briefly and admixed with 5% of the starting material solution. After the Grignard reaction had started, the remaining amount was added dropwise at such a rate that the solvent boiled on its own. After the addition was complete, the mixture was refluxed for another 3 hours and then cooled to room temperature.

47.6 g (458 mmol, 51.2 ml) of trimethyl borate were dissolved in 300 ml of THF and the solution was subsequently cooled to −78° C. The Grignard solution was then added dropwise at such a rate that the temperature did not exceed −60° C. The suspension was allowed to warm to room temperature overnight and was admixed with 250 ml of ethyl acetate. 600 g of ice water and 15 ml of concentrated $H_2SO_4$ were subsequently added and the mixture was stirred for 1 hour. The aqueous phase was extracted with 300 ml of ethyl acetate, the combined organic phases were washed with saturated NaCl solution, dried over $Na_2SO_4$ and evaporated under reduced pressure.

The solid was dissolved in 600 ml of chloroform, 31.7 ml (563 mmol) of ethylene glycol and 1.5 ml of concentrated $H_2SO_4$ were added and the mixture was refluxed on a water separator for a total of 10 hours. The solvent was removed under reduced pressure. The substance was suspended in mixture of 60 ml of water and 540 ml of ethylene glycol and stirred for one hour.

The mixture was filtered and the residue was washed with methyl t-butyl ether. The substance was suspended in 500 ml of methyl t-butyl ether and refluxed for 3 hours. The mixture was allowed to stand overnight, the solid was filtered off and washed with methyl t-butyl ether. The solid was resuspended in 500 ml of methyl t-butyl ether and refluxed for 2 hours. The mixture was allowed to stand overnight, the solid was filtered off and washed with methyl t-butyl ether. Drying under reduced pressure gave 85.7.3 g (107.1 mmol, 58%) of the ethylene glycol ester of 2',3',6',7'-tetra(2-methylbutyloxy)spirobifluorene-2,7-bisboronic acid as a white solid which, according to HPLC (Zorbax SB-C18.3.5 μm, 4.6×75 mm, 98% acetonitrile/2% ethylene glycol, 1 ml/min, UV detection 230-330 nm), had a purity of >99.8%.

$^1$H NMR ($CDCl_3$, 400 MHz): 7.56 (d, 2 H, H4/5, J=7.4 Hz); 7.82 (d, 2 H, H3/6, J=7.6 Hz); 7.20 (s, 2H, H1/8); 7.17 (s, 2H, H4'/5'); 6.07 (br. s, 2H, H1'/8'); 4.27 (s, 8H, ethylene glycol); 3.97-3.85 (m, 4H, 2×$OCH_2$); 3.53-3.38 (m, 4H, 2×$OCH_2$); 2.00-1.89 (m, 2H, C—H); 1.92-1.60 (m, 4H, C—H, $CH_2$); 1.48-1.38 (m, 2H, $CH_2$); 1.35-1.27 (m, 2H, $CH_2$); 1.17-1.07 (m, 2H, $CH_2$); 1.07 (d, 6H, 2×$CH_3$, J=6.7 Hz); 0.97 (t, 6H, 2×$CH_3$, J=7.5 Hz); 0.93 (d, 6H, 2×$CH_3$, J=6.7 Hz); 0.82 (t, 6H, 2×$CH_3$, J=7.4 Hz).

Preparation of 2,7-dibromo-2',7'-di-tert-butylspirobifluorene (M3)

200 g (579.1 mmol) of 2-bromo-4,4'-di-tert-butylbiphenyl (the preparation of this compound is described in Org. Prep. Proced. Int. 1983, 15, 271, and in J. Org. Chem. 1979, 44, 3037) were dissolved in 400 ml of distilled THF. 14.55 g (598.5 mmol) of magnesium turnings and a few crystals of iodine were placed in a reaction vessel. These were heated briefly and 5% of the amount of starting materials in THF was then added. After the reaction had started, the remainder was added at such a rate that the reaction mixture refluxed on its own without further heating (one hour). The mixture was then refluxed for 2 hours and the liquid was decanted off from the remaining magnesium. The solution was cooled to 0° C. and, while stirring vigorously, a suspension of 195.75 g (579.1 mmol) of 2,7-dibromofluoren-9-one in 1 l of THF was added dropwise over a period of 40 minutes. The ice bath was removed and the mixture was then refluxed for 90 minutes. The reaction mixture was poured onto 1800 g of ice and 45 ml of concentrated HCl and stirred until the ice had melted. The organic phases were washed twice with 30 ml each time of saturated NaHCO$_3$, then twice with 100 ml each time of water, dried over sodium sulfate and evaporated. This gave 379 g of a light-brown oil which was directly reacted further.

This oil was heated to boiling with 800 ml of acetic acid and 9.0 ml of concentrated hydrochloric acid under nitrogen. After 2 hours the mixture was cooled, the solid which had precipitated was filtered off and washed with acetic acid (200 ml) and water (300 ml). The solid was stirred with methanol, filtered off and dried. It was recrystallized twice from 1,4-dioxane. Drying at 120° C. under reduced pressure gave 229 g (390.5 mmol, 67%) of 2,7-dibromo-2',7'-di-tert-butylspirobifluorene as a colorless solid which, according to HPLC (Zorbax SB-C18 3.5 µm, 4.6×75 mm, 85% methanol/10% THF/5% water, 1 ml/min, UV detection 290-320 nm), had a purity of >99.8%.

$^1$H NMR (CDCl$_3$, 400 MHz): 7.70 (dd, 2 H, H4/5, J=8.1, 0.6 Hz); 7.67 (d, 2 H, H4'/5', J=8.1 Hz); 7.48 (dd, 2H, H3/H6, J=8.3, 1.8 Hz); 7.41 (dd, 2H, H3'/H6', J=8.1, 1.6 Hz); 6.83 (d, 2H, H1/8, J=1.6 Hz); 6.62 (d, 2H, H1'/8', J=1.3 Hz); 1.18 (s, 18 H, t-butyl).

Preparation of 2,7-di-t-butyl-2',7'-di(trimethylsilyl)spirobifluorene 50 g (85.2 mmol) of 2,7-dibromo-2',7'-di-t-butylspirobifluorene were dissolved in 450 ml of distilled THF and the solution was cooled to –78° C. 85.2 ml (213 mmol) of a 2.5M solution of butyllithium in hexane was slowly added dropwise. The mixture was stirred at this temperature for one hour, and a solution of 23.14 g (213 mmol, 27 ml) of chlorotrimethylsilane in 50 ml of distilled THF was then added dropwise and the mixture was warmed to room temperature overnight. The reaction solution was poured into 400 ml of ice water and 7 ml of concentrated hydrochloric acid, and the aqueous phase was extracted with 30 ml of ethyl acetate. The combined organic phases were admixed with 100 ml of ethyl acetate and washed three times with 100 ml each time of NaHCO$_3$ solution. The organic phase was dried over MgSO$_4$, freed of the solvent and the residue (61.12 g) was recrystallized from ethyl acetate. This gave 41.82 g (73.0 mmol, 86%) of 2,7-di-t-butyl-2',7'-bis(trimethylsilyl)spirobifluorene as a colorless solid which, according to $^1$H NMR, had a purity of >99%.

$^1$H NMR (CDCl$_3$, 400 MHz): 7.83 (dd, 2 H, H4/5, J=8.1, 0.7 Hz); 7.72 (d, 2 H, H4'/5', J=8.0 Hz); 7.51 (dd, 2H, H3/H6, J=7.5, 1.3 Hz); 7.37 (dd, 2H, H3'/H6', J=8.0, 1.6 Hz); 6.79 (d, 2H, H1/8, J=1.6 Hz); 6.72 (d, 2H, H1'/8', J=1.3 Hz); 1.13 (s, 18H, t-butyl); 0.09 (s, 18 H, CH$_3$—Si).

Preparation of the glycol ester of 2',7'-di-t-butylspirobifluorene-2,7-bisboronic acid (M4)

30.0 g (52.3 mmol) of 2,7-di-t-butyl-2',7'-bis(trimethylsilyl)spirobifluorene were dissolved in 100 ml of dry methylene chloride under N$_2$ and the solution was cooled to –78° C. and admixed with 39.3 g (157 mmol, 3 eq, 14.8 ml) of boron tribromide. The mixture was warmed overnight to room temperature, admixed with a further 100 ml of methylene chloride and poured into 500 ml of water/40 g of NaOH. The white precipitate formed was dried under reduced pressure. The precipitate was dissolved in 150 ml of chloroform, admixed with 10.1 ml (162.9 mmol) of ethylene glycol and 0.2 ml of concentrated H$_2$SO$_4$ and refluxed for 5 hours. The solid formed on cooling was filtered off with suction and recrystallized from chloroform. This gave 20.1 g (35.4 mmol, 67%) of the glycol ester of 2',7'-di-t-butyl-spirobifluorene-2,7-bisboronic acid as a colorless solid which, according to $^1$H NMR, had a purity of >99%.

$^1$H NMR (CDCl$_3$, 400 MHz): 7.90 (dd, 2 H, H4/5, J=8.1, 0.7 Hz); 7.84 (dd, 2 H, H4'/5', J=7.5, 1.0 Hz); 7.66 (d, 2H, H3/H6, J=8.0 Hz); 7.33 (dd, 2H, H3'/H6', J=8.0, 2.0 Hz); 7.17 (br. s, 2H, H1/8); 6.57 (d, 2H, H1'/8', J=1.6 Hz); 4.26 (s, 8H, ethylene glycol ester); 1.13 (s, 18 H, t-butyl).

A2: Monomers for Units of the Formula (II) (Fluorenes)

EXAMPLE M5/M6

Preparation of 2,7-dibromo-9-(2,5-dimethylphenyl)-9-[4-(3,7-dimethyloctyloxy)phenyl]fluorene and the corresponding bisboronic ester i) Preparation of 2,7-dibromo-9-(2,5-dimethylphenyl)fluoren-9-ol ii) Preparation of 2,7-dibromo-9-(2,5-dimethylphenyl)-9-(4-hydroxyphenyl)fluorene iii) Preparation of 2,7-dibromo-9-(2,5-dimethylphenyl)-9-[4-(3,7-dimethyloctyloxy)phenyl]fluorene (M5)

iv) Grignard reaction of 2,7-dibromo-9-(2,5-dimethylphenyl)-9-[4-(3,7-dimethyloctyloxy)phenyl]fluorene to form the bis(ethylene glycol) ester of 9-(4-(3,7-dimethyloctyloxy)phenyl)-9-(2,5-dimethylphenyl)fluorene-2,7-bisboronic acid (M6)

The preparation of these monomers is described in WO 00/22026

EXAMPLE M7/M8

Preparation of 2,7-dibromo-9-(2',5'-dimethylphenyl)-9-[3",4"-bis(2-methylbutyloxy)phenyl]fluorene and the Corresponding bisboronic ester Preparation of 2,7-dibromo-9-(25'-dimethylphenyl)-9-(3",4'-bishydroxyphenyl)fluorene 99.17 g (900.6 mmol) of catechol and 200.0 g (450.3 mmol) of 2,7-dibromo-9-(2,5-dimethylphenyl)-9-hydroxyfluorene were dissolved in 700 ml of toluene. The white suspension was heated to 60° C. After addition of 2.39 g (22.5 mmol, 1.96 ml) of 3-mercaptopropionic acid, 81.7 ml of concentrated H$_2$SO$_4$ (150.4 g, 1533 mmol) were slowly added dropwise over a period of 25 minutes without further heating. The suspension was stirred for another 2 hours at 60-65° C. The solid which had precipitated was filtered off with suction, dissolved in 500 ml of ethyl acetate and stirred with 1200 ml of saturated Na$_2$CO$_3$ solution. The phases were separated and the organic phase was shaken with saturated Na$_2$CO$_3$ solution until catechol was no longer present. The organic phase was then shaken twice with 200 ml each time of water and subsequently evaporated on a rotary evaporator. The residue was recrystallized from hexane/ethyl acetate. This gave 201.2 g (375.2 mmol, 83%) of 2,7-dibromo-9-(2",5'-dimethylphenyl)-9-(3",4"-bishydroxyphenyl)fluorene as a colorless solid. According to $^1$H NMR, the purity was >99%.

$^1$H NMR (d6-DMSO, 500 MHz): 8.87 (br. s, 2 H, 2×OH); 7.90 (d, 2 H, H4/H5, J=8.1 Hz); 7.59 (dd, 2 H, H3/H6, J=8.0, 1.6 Hz); 7.41 (d, 2 H, H1, H8, J=1.5 Hz); 6.98-6.94 (m, 2H, H5', H6'); 6.89 (br. s, 1H, H6'); 6.64 (d, 1H, H3", J=8.3 Hz); 6.56 (d, 1H, H6", J=2.3 Hz); 6.43 (dd, 1H, H4", J=8.3, 2.3 Hz); 2.16 (s, 3H, CH$_3$ on C5"); 1.42 (br. s, 3H, CH$_3$ on C2").

Preparation of 2,7-dibromo-9-(2',5'-dimethylphenyl)-9-[3", 4"-bis(2-methylbutyloxy)phenyl]fluorene (M7)

76.1 g (550 mmol, 2.2 eq) of milled potassium carbonate were suspended in 270 ml of dry dimethylformamide. 134.1 g (250 mmol) of 2,7-dibromo-9-(2,5-dimethylphenyl)-9-(3, 4-dihydroxyphenyl)fluorene were added a little at a time and 154.6 g (600 mmol, 2.4 eq) of 1-toluenesulfonyloxy-2-methylbutane were added dropwise over a period of 20 minutes. The mixture was heated at 85° C. for 18 hours. A further 25.5 g of potassium carbonate and 51.6 g (200 mmol) of 1-toluenesulfonyloxy-2-methylbutane were added and the mixture was heated for a further 30 hours. The reaction mixture was cooled and the product which had precipitated was filtered off with suction and washed with hexane. The white solid was stirred 4 times with 200 ml each time of ethanol and dried. Recrystallization from 1,4-dioxane gave 169.3 g (197.6 mmol, 79%) of 2,7-dibromo-9-(2',5'-dimethylphenyl)-9-[3",4"-bis(2-methylbutyloxy)phenyl]fluorene (M7) as a colorless solid.

$^1$H NMR (CDCl$_3$, 500 MHz): 7.56 (2 H, H4/H5, J=8.3 Hz); 7.46 (d, 2 H, H3/H6, J=8.1 Hz); 7.55-7.35 (br. m, 2 H, H1/H8); 6.98 and 6.93 (2×d, each 1H, H3'/H4', J=7.5 Hz), 6.94 (br. s, 1H, H6'); 6.84 (d, 1H, H2", J=2.3); 6.65 (d, 1H, H5", J=8.3 Hz); 6.52 (dd, 1H, H6", J=8.3.2.3 Hz); 3.8-3.6 (m, 4H, OCH$_2$); 2.21 (s, 3H, CH$_3$ on C5'); 1.90-1.77 (m, 2H, H—C); 1.60-1.48 (m, 2H, CH$_2$); 1.47 (br. s, 3H, CH$_3$ on C2');1.30-1.18 (m, 2H, CH$_2$); 1.01-0.88 (m, 12H, 4×CH$_3$).

Preparation of bis(pinacolyl) 9-(3",4"-bis(2-methylbutyloxy)phenyl)-9-(2,5'-dimethylphenyl)fluorene-2,7-bisboronate (M8)

92.0 g (136 mmol) of 2,7-dibromo-9-(3",4"-bis(2-methylbutyloxy)phenyl)-9-(2',5'-dimethylphenyl)fluorene were dissolved in 250 ml of THF. 6.96 g (286 mmol) of Mg were placed in a reaction vessel, a spatula tip of iodine was added and 10% of the amount of the starting material solution was then added. After the reaction had started, the remaining solution was added dropwise over a period of half an hour and the mixture was then refluxed for another 3 hours.

76.0 g (408 mmol, 83.4 ml) of isopropyl pinacolyl borate were dissolved in 200 ml of THF and the solution was cooled to −70° C. The Grignard solution was added dropwise over a period of one hour, the mixture was stirred at −70° C. for another 3 hours and then thawed overnight.

At room temperature, firstly 65.34 g (62.3 ml, 1088 mmol) of acetic acid in 250 ml of water and then 200 ml of ethyl acetate were subsequently added. The organic phase was washed with 100 ml of water, dried over MgSO$_4$ and evaporated on a rotary evaporator. This gave 89.2 g of crude product which was recrystallized from n-hexane/isopropanol. This resulted in 82.6 g (107.2 mmol, 78%) of a solid which, according to $^1$H NMR and HPLC (Zorbax SB-C18 3.5 µm, 4.6×75 mm, 98% acetonitrile/2% pinacol, 1 ml/min, UV detection 230-330 nm), had a purity of >99.8%.

$^1$H NMR (CDCl$_3$, 500 MHz): 7.92-7.63 (m, 6 H, H-fluorene); 7.08 (d, 1 H, H2", J=2.4); 7.05 (br. s, 1H, H6'), 6.95 and 6.86 (2×d, each 1H, H3'/H4', J=7.7), 6.60-6.54 (m, 2H, H5", H6"); 3.8-3.6 (m, 4H, OCH$_2$); 2.23 (s, 3H, CH$_3$—C5'); 1.94-1.77 (m, 2H, C—H); 1.59-1.48 (m, 2H, CH$_2$); 1.31 (br. s, 3H, CH$_3$ on C2');1.28-1.18 (m, 2H, CH$_2$); 1.00-0.85 (m, 12H, 4×CH$_3$).

EXAMPLE M14/M15

Preparation of 2,7-dibromo-9,9-bis(2-ethylhexyl)fluorene and the corresponding bisboronic ester The preparation of 2,7-dibromo-9,9-bis(2-ethylhexyl) fluorene (M14) and the bisglycol ester of 9,9-bis(2-ethyl hexyl)fluorene-2,7-bisboronic acid (M15) is described in WO 00/22027.

A3: Monomers for Units of the Formulae (III) to (V) (Triarylamines, Phenylenediamine Derivatives and Tetraarylbenzidines)

Preparation of N,N'-diphenyl-N,N'-bis(4-tert-butylphenyl) benzidine 30.79 g (91.53 mmol) of N,N'-diphenylbenzidine and 42.92 g (201.4 mmol) of 1-bromo-4-tert-butylbenzene were dissolved in 600 ml of distilled toluene under N$_2$ and with exclusion of light. 740.4 mg (3.66 mmol) of tris-o-tolylphosphine, 412.2 mg (1.83 mmol) of palladium acetate and 22.75 g (236.5 mmol) of NaOtBu were then added.

The suspension was heated at 90° C. for 1 hour.

After cooling to room temperature, the precipitate formed was filtered off with suction and the mother liquor was stirred with 400 ml of 1% strength NaCN solution. The aqueous phase was extracted twice with 200 ml each time of ethyl acetate, and the combined organic phases were washed twice with 100 ml each time of water. The organic phase was dried over Na$_2$SO$_4$ and the solvent was removed on a rotary evaporator. The solid obtained was stirred with hexane and recrystallized from ethyl acetate. This gave 28.98 g (48.2 mmol, 53%) of N,N'-diphenyl-N,N'-bis(4-tert-butyl)phenylbenzidine as a colorless solid which, according to HPLC (Zorbax SB-C18 3.5 µm, 4.6×75 mm, 85% methanol/10% THF/5% water, 1 ml/min, UV detection 280-380 nm), had a purity of >99.9%.

$^1$H NMR (CDCl$_3$+N$_2$H$_4$.H$_2$O, 500 MHz): 7.43 (d with FS, 4H, H-arom, J=8.7 Hz); 7.32-7.21 (m, 8H, H-arom); 7.13-7.08 (m, 8H, H-arom); 7.04 (d with FS, 4H, H-arom, J=8.6 Hz); 7.01-6.96 (m, 2H, H-arom); 1.32 (s, 18H, t-butyl).

Preparation of N,N'-diphenyl-N,N'-bis(4-methoxyphenyl) benzidine

Using a method analogous to the preceding example, 10 g (29.72 mmol) of N,N'-diphenylbenzidine, 12.23 g (65.4 mmol) of 1-bromo-4-methoxybenzene were reacted with 362 mg (1.19 mmol) of tris-o-tolylphosphine, 7.43 g (77.4 mmol) of NaOtBu and 132 mg (0.58 mmol) of palladium acetate in 200 ml of distilled toluene. Analogous work-up and recrystallization from hexane gave 12.7 g (73%) of a solid which, according to HPLC (Zorbax SB-C18 3.5 µm, 4.6×75 mm, 85% methanol/10% THF/5% water, 1 ml/min, UV detection 280-380 nm), had a purity of >99.8%.

$^1$H NMR (CDCl$_3$+N$_2$H$_4$.H$_2$O, 500 MHz): 7.41 (d with FS, 4H, H-aromatic, J=8.7 Hz); 7.25-7.20 (m, 4H, H-aromatic); 7.12-7.05 (m, 12H, H-aromatic); 6.98-6.92 (m, 2H, H-aromatic); 6.85 (d with FS, 4H, H-aromatic, J=8.6 Hz); 3.81 (s, 6H, OCH$_3$).

Preparation of N,N'-bis(4-bromophenyl)-N,N'-bis(4-tert-butylphenyl)benzidine (M9)

10.57 g (17.59 mmol) of N,N'-diphenyl-N,N'-bis(4-tert-butylphenyl)benzidine were dissolved in 100 ml of chloroform, admixed with one drop of hydrazine hydrate and cooled to 0° C. 6.26 g (35.18 mmol, 2 eq) of N-bromosuccinimide were then added a little at a time over a period of 15 minutes. The mixture was stirred at this temperature for another 20 minutes. The precipitate formed was filtered off with suction and the mother liquor was washed with 100 ml of saturated Na$_2$SO$_3$ solution. The aqueous phase was extracted with 100 ml of chloroform and the combined organic phases were washed twice with 100 ml each time of water and dried over MgSO$_4$. Taking off the solvent and recrystallization from ethyl acetate gave 10.45 g (13.8 mmol, 78%) of N,N'-bis(4-bromophenyl)-N,N'-bis(4-tert-butylphenyl)benzidine as a colorless solid which, according to HPLC (Zorbax SB-C18 3.5 µm, 4.6×75 mm, 85% methanol/10% THF/5% water, 1 ml/min, UV detection 280-380 nm), had a purity of >99.8%.

$^1$H NMR (CDCl$_3$+N$_2$H$_4$*H$_2$O, 500 MHz): 7.43 (d with FS, 4H, H-aromatic, J=8.7 Hz); 7.32 (d with FS, 4H, H-aromatic, J=8.7 Hz); 7.28 (d with FS, 4H, H-aromatic, J=8.7 Hz); 7.09 (d with FS, 4H, H-aromatic, J=8.7 Hz); 7.03 (d with FS, 4H, H-aromatic, J=8.7 Hz); 6.97 (d with FS, 4H, H-aromatic, J=8.7 Hz); 1.32 (s, 18H, t-butyl).

Preparation of N. N'-bis(4-bromophenyl)-N,N'-bis(4-methoxyphenyl)benzidine (M10)

Using a method analogous to the preceding preparation, 12.6 g (22.96 mmol) of N,N'-diphenyl-N,N'-bis(4-methoxyphenyl)benzidine in 350 ml of chloroform were reacted with 10.62 g (59.7 mmol, 2 eq) of N-bromosuccinimide and recrystallized from ethyl acetate. This gave 9.81 g (13.9 mmol, 60%) of N,N'-bis(4-bromophenyl)-N,N'-bis(4-methoxyphenyl)benzidine as a colorless solid M10 which, according to HPLC (Zorbax SB-C18 3.5 µm, 4.6×75 mm, 85% methanol/10% THF/5% water, 1 ml/min, UV detection 280-380 nm), had a purity of >99.5%.

$^1$H NMR (CDCl$_3$+N$_2$H$_4$.H$_2$O, 500 MHz): 7.40 (d with FS, 4H, H-aromatic, J=9.0 Hz); 7.30 (d with FS, 4H, H-aromatic, J=9.0 Hz); 7.07 and 7.05 (2×d with FS, each 4H, H-aromatic, J~8 Hz); 6.92 (d with FS, 4H, H-aromatic, J=8.7 Hz); 6.85 (d with FS, 4H, H-aromatic, J=8.7 Hz); 3.80 (s, 6H, OCH$_3$).

Preparation of 4,4'-dibromotriphenylamine (M11)

The synthesis of this compound is described in DE 19 981 010.

A4: Monomers for Units of the Formulae (VI) to (XXXXV)

Preparation of 4,7-dibromobenzo[1,2,5]thiadiazole (M12)

The preparation of this compound is described in J. Heterocycl. Chem. 1970, 629-633.

Preparation of 4,7-dibromobenzofurazone (M13)

The preparation of this compound is described in J. Chem. Soc. 1931, 3308-3311.

To provide a better overview, the structural formulae of the monomers whose syntheses have been described here are shown below.

M1
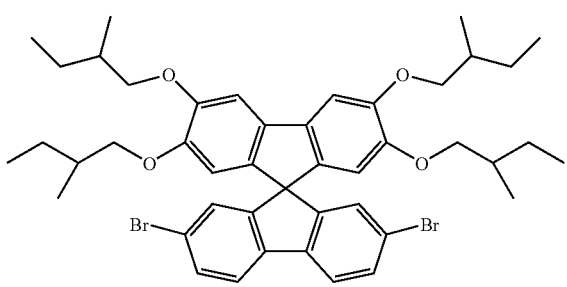

-continued

M2
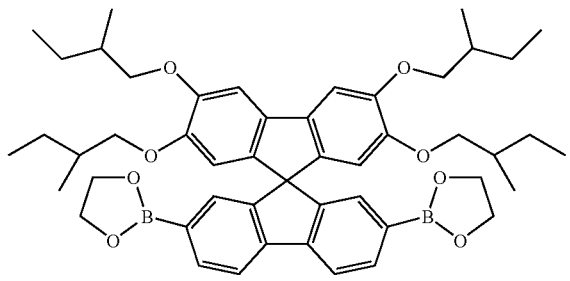

M3
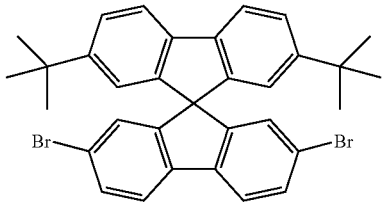

M4
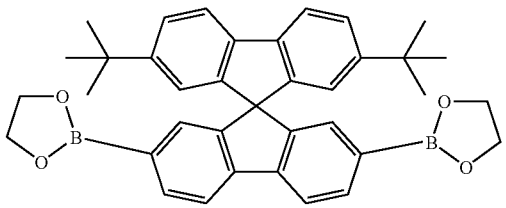

M5
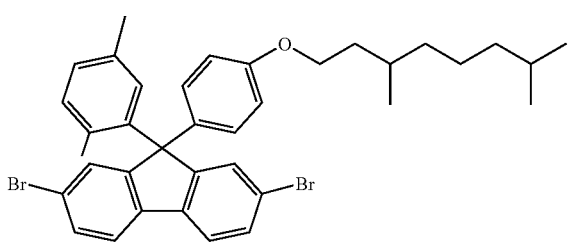

M6
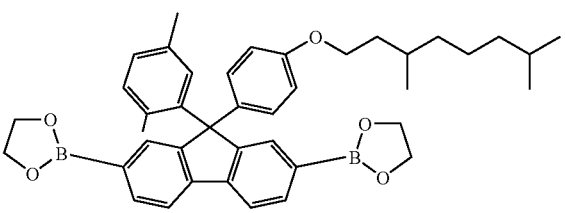

M7
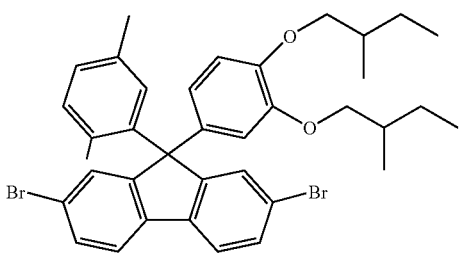

-continued
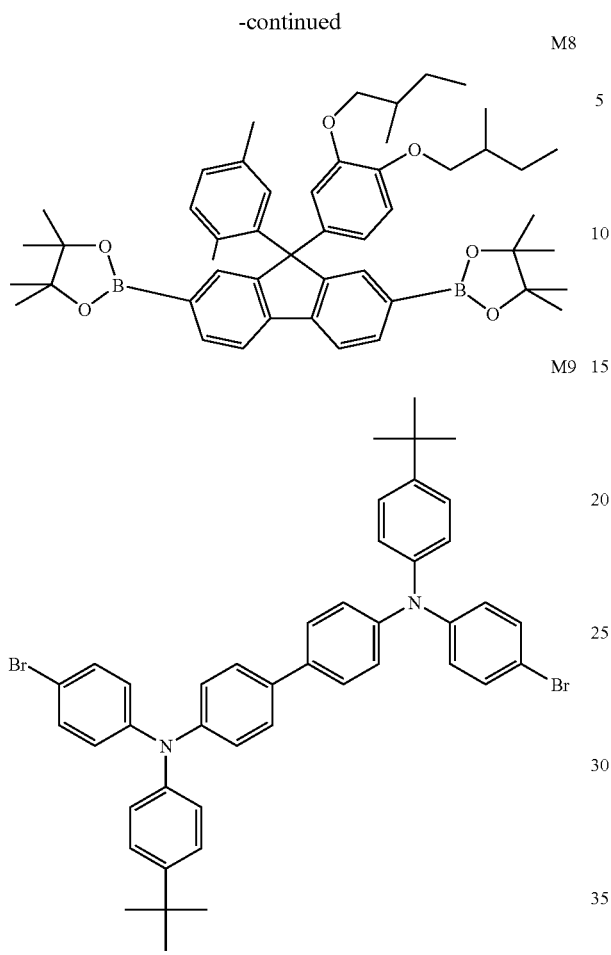
M8
M9
M10
M11
-continued
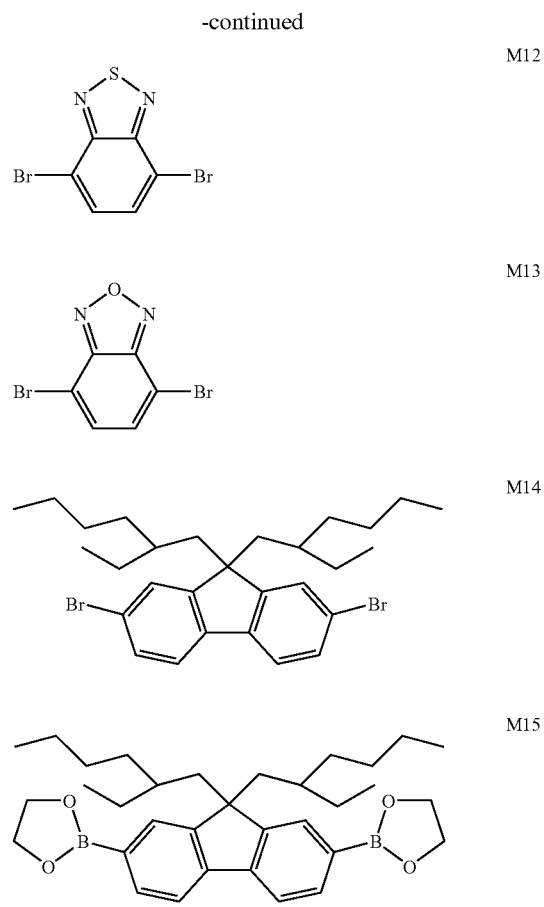
M12
M13
M14
M15
Further monomers were prepared by analogous methods or as described in the above-cited references. These are shown below:
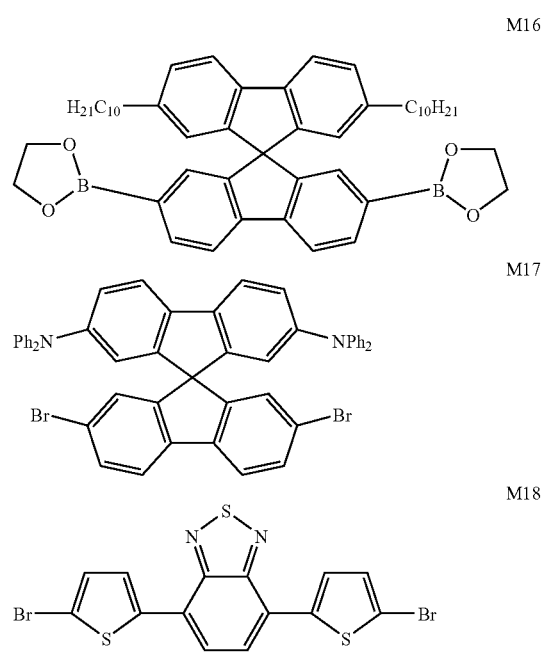
M16
M17
M18

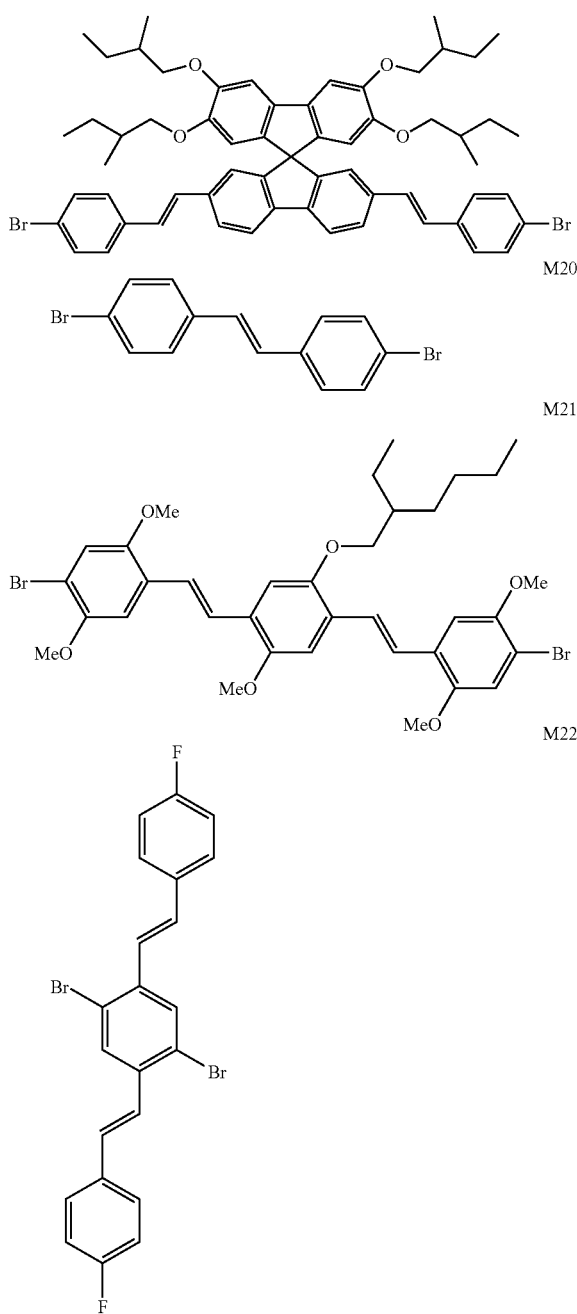

Part B: Preparation of the Polymers

EXAMPLE P1

Copolymerization of 50 mol % of 2,7-dibromo-2', 3', 6',7'-tetra(2-methylbutyloxy)spirobifluorene (M1), 40 mol % of 2,7-dibromo-9-(2',5'-dimethylphenyl)-9-[3",4"-bis(2-methylbutyloxy)phenyl] fluorene (M7) and 10 mol % of N,N'-bis(4-bromo)phenyl-N,N'-bis(4-tert-butyl)phenylbenzidine (M9) by Yamamoto coupling (polymer P1)

25 ml of dimethylformamide and 80 ml of toluene were heated to 80° C. under argon, and 1.53 g (5.57 mmol) of Ni(COD)$_2$ and 0.87 g (5.57 mmol) of 2,2'-bipyridyl were then added. After 30 minutes, firstly 0.379 g (3.51 mmol, 0.43 ml) of 1,5-cyclooctadiene and then a solution of 0.990 g (1.21 mmol) of 2,7-dibromo-2',3',6',7'-tetra(2-methylbutyloxy)spirobifluorene, 0.652 g (0.968 mmol) of 2,7-dibromo-9-(2',5'-dimethylphenyl)-9-[3",4"-bis(2-methylbutyloxy) phenyl]fluorene and 0.183 g (0.242 mmol) of N,N'-bis(4-bromo)phenyl-N,N'-bis(4-tert-butyl)phenylbenzidine in 20 ml of toluene were added. After 144 hours, the mixture was cooled, 5 ml of HCl in dioxane were added and the reaction mixture was stirred for 15 minutes. 50 ml of chloroform were added and the mixture was stirred for 15 minutes. The organic phase was washed twice with 100 ml each time of 5M HCl and once with 100 ml of saturated NaHCO$_3$ solution. The solution was precipitated in 450 ml of methanol and the crude polymer was filtered off with suction. It was reprecipitated twice from, each time, 100 ml of THF/ 150 ml of methanol. This gave 0.90 g (63%) of fibrous, light-yellow polymer P1.

$^1$H NMR (CDCl$_3$): 7.8-7.7 (m, 1 H, spiro); 7.7-7.1 (m, 10.7 H, fluorene, spiro, TAD); 6.6 (br. s, 0.8H, fluorene), 6.21 (m, 1H, spiro); 4.0-3.4 (3×m, 5.6H, OCH$_2$), 2.16 (s, 1.2H, CH$_3$); 1.9-0.7 (m, alkyl H, including t-butyl at 1.30).

GPC: THF; 1 ml/min, Plgel 10 µm Mixed-B 2×300×7.5 mm$^2$, 35° C., RI detection: Mw=180000 g/mol, Mn=79000 g/mol

EXAMPLE P2

Copolymerization of the ethylene glycol ester of 2',3',6',7'-tetra(2-methylbutyloxy)spirobifluorene-2, 7-bisboronic Acid (M2), 2,7-dibromo-9-(2',5'-dimethylphenyl)-9-[3",4"-bis(2-methylbutyloxy)phenyl] fluorene (M7) and 12.5 mol % of N,N'-bis(4-bromophenyl)-N,N'-bis(4-tert-butylphenyl)benzidine (M9) by the Suzuki reaction (polymer P2).

5.0740 g (7.500 mmol) of 2,7-dibromo-9-(2',5'-dimethylphenyl)-9-[3",4"-bis(2-methylbutyloxy)phenyl]fluorene, 8.0065 g (10.00 mmol) of the ethylene glycol ester of 2',3',6',7'-tetra(2-methylbutyloxy)spirobifluorene-2,7-bisboronic acid, 1.8966 g (2.500 mmol) of N,N'-bis(4-bromophenyl)-N,N'-bis(4-tert-butylphenyl)benzidine, 9.67 g (42 mmol) of K$_3$PO$_4$·H$_2$O, 30 ml of toluene, 15 ml of water and 0.25 ml of ethanol were degassed for 30 minutes by passing N$_2$ through the mixture. 175 mg (0.15 mmol) of Pd(PPh$_3$)$_4$ were subsequently added under protective gas. The suspension was stirred vigorously at an internal temperature of 87° C. under a blanket of N$_2$ (gentle reflux). After 4 days, a further 0.30 g of the ethylene glycol ester of 2',3',6',7'-tetra (2-methylbutyloxy)spirobifluorene-2,7-bisboronic acid were added. After heating for a further 6 hours, 0.3 ml of bromobenzene were added and the mixture was refluxed for another 3 hours.

The reaction solution was diluted with 200 ml of toluene and stirred with 200 ml of 2% strength aqueous NaCN for 3 hours. During this time, the mixture became virtually colorless. The organic phase was washed with H$_2$O and the polymer was precipitated by addition to 800 ml of ethanol. The polymer was dissolved in 200 ml of THF at 40° C. for 1 hour, precipitated by means of 250 ml of MeOH, washed and dried under reduced pressure. It was reprecipitated in 200 ml of THF/250 ml of methanol one more time, filtered off with suction and dried to constant mass. This gave 10.03 g (16.7 mmol, 84%) of the polymer P2 as a light-yellow solid.

$^1$H NMR (CDCl$_3$): 7.8-7.7 (m, 1 H, spiro); 7.7-7.1 (m, 10.75 H, fluorene, spiro, TAD); 6.6 (br. s, 0.75H, fluorene), 6.21 (m, 1H, spiro); 4.0-3.4 (3×m, 5.5 H, OCH$_2$), 2.16 (s, 1.125 H, CH$_3$); 1.9-0.7 (m, alkyl H, including t-butyl at 1.30).

GPC: THF; 1 ml/min, PLgel 10 μm Mixed-B 2×300×7.5 mm$^2$, 35° C., RI detection: Mw=67000 g/mol, Mn=29000 g/mol.

Further polymers were prepared by methods analogous to those described for P1 and P2. The chemical properties are summarized in the table below. A number of comparative polymers (which each comprise either only units of the formula (I) or units of the formula (II) or may further comprise additional units) were also prepared. These, too, are shown in the table. All these polymers were examined for use in PLEDs. The manner in which PLEDs can be produced has been mentioned above and is described in more detail in part C.

The most important device properties (color, efficiency and life) are also shown in the table.

device). The LEDs described below were each two-layer systems, i.e. substrate//ITO//PEDOT//polymer//cathode.

PEDOT is a polythiophene derivative.

General Method of Producing High-efficiency, Long-life LEDs:

After the ITO-coated substrates (e.g. glass supports, PET film) have been cut to the correct size, they are cleaned in a number of cleaning steps in an ultrasonic bath (e.g. soap solution, Millipore water, isopropanol).

They are dried by blowing with an N$_2$ gun and are stored in a dessicator. Before being coated with the polymer, they are treated by means of an ozone plasma apparatus for about 20 minutes. A solution of the respective polymer is then made up (generally a solution having a concentration of 4-25 mg/ml in, for example. toluene, chlorobenzene, xylene: cyclohexanone (4:1)) and the polymer is dissolved at room temperature by stirring. Depending on the polymer, it may be advantageous to stir at 50-70° C. for some time. When the polymer has been dissolved completely, the solution is filtered through a 5 μm filter and applied at variable speeds (400-6000) using a spin coater. The layer thicknesses can in this way be varied in a range from about 50 to 300 nm. A

| | Proportion of the monomers in the polymerization [%] | | | | GPC** | | Electroluminescence*** | | | | Visco.**** |
|---|---|---|---|---|---|---|---|---|---|---|---|
| Polymer (type)* | Monom. 1 | Monom. 2 | Monom. 3 | Monom. 4 | M$_w$ (–1000 g/mol) | M$_N$ (–1000 g/mol) | λ$_{max}$ [nm] | Max. Eff [Cd/A] | Voltage at 100 Cd/m$^2$ [V] | Life at 100 Cd/m$^2$ [hours] | Gel temp. [° C.] |
| P1 (Y) | 50% M1 | 40% M7 | 10% M9 | | 180 | 79 | 468 | 2.5 | 4.2 | 800 | <0° C. |
| P2 (S) | 50% M2 | 37.5% M7 | 12.5% M9 | | 67 | 29 | 467 | 2.3 | 4.6 | 650 | <0° C. |
| P3 (S) | 50% M2 | 40% M7 | 10% M9 | | 73 | 33 | 466 | 1.8 | 5.2 | 390 | <0° C. |
| P4 (S) | 50% M2 | 30% M7 | 20% M9 | | 95 | 36 | 469 | 1.5 | 5.8 | 200 | <0° C. |
| P5 (S) | 50% M2 | 10% M7 | 40% M9 | | 56 | 24 | 473 | 0.4 | 7.3 | 100 | <0° C. |
| P6 (S) | 50% M2 | 50% M7 | | | 79 | 40 | 458 | 0.3 | 7.3 | 100 | <0° C. |
| P7 (Y) | 50% M1 | 50% M7 | | | 170 | 82 | 457 | 0.4 | 7.1 | 100 | <0° C. |
| P8 (S) | 50% M4 | 40% M7 | 10% M9 | | 73 | 34 | 467 | 1.9 | 5.3 | 450 | 10° C. |
| P9 (S) | 50% M2 | 40% M7 | 10% M10 | | 63 | 29 | 469 | 1.6 | 5.6 | 330 | <0° C. |
| P10 (S) | 50% M2 | 40% M7 | 10% M11 | | 59 | 28 | 466 | 1.3 | 6.4 | 230 | <0° C. |
| P11 (S) | 50% M2 | 40% M5 | 10% M9 | | 78 | 39 | 468 | 1.7 | 5.5 | 290 | <0° C. |
| P12 (S) | 50% M2 | 40% M7 | 10% M9 | | 73 | 33 | 466 | 1.8 | 5.2 | 390 | <0° C. |
| P13 (S) | 50% M2 | 30% M7 | 10% M9 | 10% M12 | 82 | 38 | 550 | 6.5 | 4.9 | 800 | <0° C. |
| P14 (S) | 50% M2 | 30% M7 | 10% M9 | 10% M13 | 76 | 32 | 575 | 5.9 | 5.3 | 600 | <0° C. |
| P15 (S) | 50% M2 | 40% M7 | 10% M22 | | 500 | 230 | 455 | 1.3 | 6.0 | 700 | <0° C. |
| P16 (S) | 50% M2 | 30% M7 | 20% M17 | | 750 | 215 | 459 | 1.7 | 5.5 | 400 | <0° C. |
| P17 (S) | 50% M2 | 30% M7 | 10% M9 | 10% M19 | 450 | 100 | 462 | 4.5 | 4.0 | 2000 | <0° C. |
| P18 (S) | 50% M2 | 30% M7 | 20% M20 | | 600 | 200 | 472 | 2.8 | 4.7 | 600 | <0° C. |
| P19 (S) | 50% M2 | 20% M7 | 10% M9 | 20% M21 | 350 | 110 | 505 | 8.6 | 3.3 | 3500 | <0° C. |
| P20 (S) | 25% M2 | 25% M7 | 10% M9 | 35% M12, 5% M18 | 240 | 60 | 634 | 1.6 | 3.9 | 8500 | <0° C. |
| P21 (S) | 50% M16 | 40% M7 | 10% M9 | | 600 | 200 | 443 | 3.0 | 5.0 | 500 | <0° C. |
| V1 (S) | 50% M2 | 40% M1 | 10% M9 | | 66 | 29 | 471 | 1.2 | 6.3 | 60 | ~0° C. |
| V2 (S)$^\#$ | 50% M4 | 40% M1 | 10% M9 | | 59 | 29 | 468 | 0.9 | 7.8 | 30 | 20° C. |
| V3 (S) | 50% M4 | 40% M3 | 10% M9 | | — | — | — | — | — | — | >50° C. |
| V4 (S) | 50% M6 | 40% M5 | 10% M9 | | 73 | 33 | 471 | 0.8 | 6.9 | 8 | ~0° C. |
| V5 (S) | 50% M8 | 50% M7 | | | 85 | 40 | 459 | 0.2 | 9.5 | <2 | 10° C. |
| V6 (S) | 50% M8 | 40% M7 | 10% M9 | | 69 | 30 | 470 | 0.5 | 8.3 | 6 | 5° C. |

*S = Prepared by Suzuki polymerization (cf. Ex. P2), Y = Prepared by Yamamoto polymerization (cf. Ex. P1)
**GPC measurements in THF; 1 ml/min, Plgel 10 μm Mixed-B 2 × 300 × 7.5 mm$^2$, 35° C., RI detection was calibrated against polystyrene
***For preparation of the polymeric LEDs, see Part C
****Solutions of the polymer (10 mg/ml) in toluene were heated to 60° C., cooled at 1° C./minute and the viscosity was measured on a Brookfield LVDV-III rheometer (CP-41). At the gel temperature determined in this way, a sharp increase in the viscosity occurred.
$^\#$Owing to the poor solubility, the PLEDs were produced from chlorobenzene Part C: Production and Characterization of LEDs:

LEDs were produced by the general method outlined below. This naturally had to be adapted in each individual case according to the respective circumstances (e.g. polymer viscosity and optimum thickness of the polymer layer in the conductive polymer, preferably doped PEDOT or PANI, is usually applied beforehand to the (structured) ITO.

Electrodes are then applied on top of the polymer films. This is generally carried out by thermal vapor deposition (Balzer BA360 or Pfeiffer PL S 500). The transparent ITO electrode is subsequently connected as the anode and the metal electrode (e.g. Ba, Yb, Ca) is connected as the cathode and the device parameters determined. The results obtained using the polymers described are summarized in the table in part B. For polymer P1, the typical IVL characteristics in a test polymeric LED are shown in FIG. 1.

What is claimed is:

1. A conjugated polymer comprising recurring units of the formula (I)

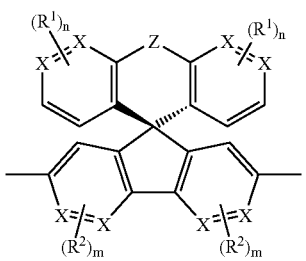

formula (I)

and recurring units of the formula (II),

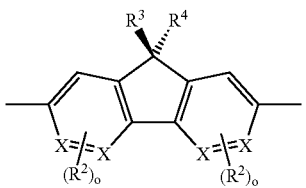

formula (II)

where the proportion of repeating units of the formula (I) and formula (II) together make up at least 20%, and the ratio of the repeating units of the formula (I) to those of the formula (II) is in the range from 1:10 to 10:1, 0 and at least one structural element which have repeating units which have structures different from those of the formula (I) or (II)

and the symbols and indices have the following meanings:

X is identical or different on each occurrence and is CH, $CR^1$ or N,

Z is identical or different on each occurrence and is a single chemical bond, a $CR^3R^4$ group, a $CR^3R^4$—$CR^3R^4$ group, a $CR^3$=$CR^4$ group, O, S, N—$R^5$, C=O, C=$CR^3R^4$ or $SiR^3R^4$;

$R^1$ is identical or different on each occurrence and is a straight-chain, branched or cyclic alkyl or alkoxy chain which has from 1 to 22 carbon atoms and in which one or more nonadjacent carbon atoms is optionally replaced by N—$R^5$, O, S, —CO—O—, or O—CO—O, where one or more H atoms is optionally replaced by fluorine, an aryl or aryloxy group which has from 5 to 40 carbon atoms and in which one or more carbon atoms is optionally replaced by O, S or N and which is optionally substituted by one or more nonaromatic radicals $R^1$, Cl, F, CN, or $N(R^5)_2$, where two or more radicals $R^1$ is optionally joined to form a ring system;

$R^2$ is identical or different on each occurrence and is a straight-chain, branched or cyclic alkyl or alkoxy chain which has from 1 to 22 carbon atoms and in which one or more nonadjacent carbon atoms is optionally replaced by N—$R^5$, O, S, —CO—O—, or O—CO—O, where one or more H atoms is optionally replaced by fluorine, an aryl or aryloxy group which has from 5 to 40 carbon atoms and in which one or more carbon atoms is optionally replaced by O, S or N and which is optionally substituted by one or more nonaromatic radicals $R^1$, or CN;

$R^3$ and $R^4$ are identical or different on each occurrence and are each H, a straight-chain, branched or cyclic alkyl chain which has from 1 to 22 carbon atoms and in which one or more nonadjacent carbon atoms is optionally replaced by N—$R^5$, O, S, —CO—O—, or O—CO—O, where one or more H atoms is optionally replaced by fluorine, an aryl group which has from 5 to 40 carbon atoms and in which one or more carbon atoms is optionally replaced by O, S or N and which is optionally substituted by one or more nonaromatic radicals $R^1$, or CN; the two radicals $R^3$ and $R^4$ is optionally joined to form a ring which does not, however, lead to structures of the formula (I);

$R^5$ is identical or different on each occurrence and is H, a straight-chain, branched or cyclic alkyl chain which has from 1 to 22 carbon atoms and in which one or more nonadjacent carbon atoms is optionally replaced by O, S, —CO—O—, or O—CO—O, where one or more H atoms is optionally replaced by fluorine, an aryl group which has from 5 to 40 carbon atoms and in which one or more carbon atoms is optionally replaced by O, S or N and which is optionally substituted by one or more nonaromatic radicals $R^1$;

n is identical or different on each occurrence and is 0, 1, 2, 3 or 4;

m is identical or different on each occurrence and is 0, 1, 2 or 3;

o is identical or different on each occurrence and is 0, 1, 2 or 3, with the proviso that in the case of at least one unit of the formula (I), at least one index n and/or m is not.

2. The polymer as claimed in claim 1, wherein X=C—H or C—$R^1$.

3. The polymer as claimed in claim 1, wherein Z represents a single chemical bond.

4. The polymer as claimed in claim 1, wherein:

$R^1$ is identical or different on each occurrence and is a straight-chain, branched or cyclic alkyl or alkoxy chain which has from 1 to 10 carbon atoms and in which one or more H atoms is optionally replaced by fluorine, or an aryl group which has from 6 to 14 carbon atoms and which is also substituted by one or more nonaromatic radicals $R^1$.

5. The polymer as claimed in claim 1, wherein:

$R^1$ is identical or different on each occurrence and is a straight-chain or branched alkyl or alkoxy chain having from 1 to 8 carbon atoms or an aryl group which has from 6 to 10 carbon atoms and is also substituted by one or more nonaromatic radicals $R^1$; and n are identical or different and are each 1 or 2.

6. The polymer as claimed in claim 1, wherein:

$R^2$ is identical or different on each occurrence and is a straight-chain or branched alkyl or alkoxy chain which has from 1 to 10 carbon atoms and in which one or more H atoms is optionally replaced by fluorine, an aryl or aryloxy group which has from 6 to 14 carbon atoms and which is optionally substituted by one or more nonaromatic radicals $R^1$, or CN; and o and m are identical or different on each occurrence and are each 0 or 1.

7. The polymer as claimed in claim 1, wherein:

$R^2$ is identical or different on each occurrence and is a straight-chain or branched alkyl or alkoxy chain which has from 1 to 8 carbon atoms and in which one or more H atoms is optionally replaced by fluorine, or an aryl group which has from 6 to 10 carbon atoms and which is optionally substituted by one or more nonaromatic radicals $R^1$; and o and m are identical or different on each occurrence and are each 0 or 1, with o and m being 0 for at least 50%, of all repeating units of the formulae (I) and (II) present in the polymer.

8. The polymer as claimed in claim 1, wherein:
$R^3$ and $R^4$ are identical or different on each occurrence and are each a straight-chain, branched or cyclic alkyl chain which has from 1 to 10 carbon atoms and in which one or more nonadjacent carbon atoms is optionally replaced by O, where one or more H atoms is optionally replaced by fluorine, or an aryl group which has from 5 to 40 carbon atoms and in which one or more carbon atoms is optionally replaced by O, S or N and which is optionally substituted by one or more nonaromatic radicals $R^1$.

9. The polymer as claimed in claim 2, wherein:
Z represents a single chemical bond,
$R^1$ is identical or different on each occurrence and is a straight-chain or branched alkyl or alkoxy chain having from 1 to 8 carbon atoms or an aryl group which has from 6 to 10 carbon atoms and is also substituted by one or more nonaromatic radicals $R^1$;
n are identical or different and are each 1 or 2,
$R^2$ is identical or different on each occurrence and is a straight-chain or branched alkyl or alkoxy chain which has from 1 to 8 carbon atoms and in which one or more H atoms is optionally replaced by fluorine, or an aryl group which has from 6 to 10 carbon atoms and which is optionally substituted by one or more nonaromatic radicals $R^1$; and
o and m are identical or different on each occurrence and are each 0 or 1, with o and m being 0 for at least 50%, of all repeating units of the formulae (I) and (II) present in the polymer and
$R^3$ and $R^4$ are identical or different on each occurrence and are each a straight-chain, branched or cyclic alkyl chain which has from 1 to 10 carbon atoms and in which one or more nonadjacent carbon atoms is optionally replaced by O, where one or more H atoms is optionally replaced by fluorine, or an aryl group which has from 5 to 40 carbon atoms and in which one or more carbon atoms is optionally replaced by O, S or N and which is optionally substituted by one or more nonaromatic radicals $R^1$.

10. The polymer as claimed in claim 1, wherein:
$R^3$ and $R^4$ are identical or different on each occurrence and are each an aryl group which has from 6 to 14 carbon atoms and is optionally substituted by one or more nonaromatic radicals $R^1$.

11. The polymer as claimed in claim 1, wherein:
$R^3$ and $R^4$ are identical or different on each occurrence and are each an aryl group which has from 6 to 14 carbon atoms and which is optionally substituted by one or more nonaromatic radicals $R^1$ and in which the substituents $R^3$ and $R^4$ are different from one another on a unit of the formula (II).

12. The polymer as claimed in claim 9, wherein:
$R^3$ and $R^4$ are identical or different on each occurrence and are each an aryl group which has from 6 to 14 carbon atoms and which is optionally substituted by one or more nonaromatic radicals $R^1$ and in which the substituents $R^3$ and $R^4$ are different from one another on a unit of the formula (II).

13. The polymer as claimed in claim 1, wherein said at least one structural element has charge transport properties.

14. A polymer as claimed in claim 13, wherein said least one structural element has hole transport properties.

15. The polymer as claimed in claim 13, wherein said at least one structural element is a triarylamine derivative, a benzidine derivative, a tetraarylene-para-phenylenediamine derivative, a phenothiazine derivative, a phenoxazine derivative, a dihydrophenazine derivative, a thianthrene derivative, a benzo-p-dioxin derivative, a phenoxathiine derivative, a carbazole derivative, an azulene derivative, a thiophene derivative, a pyrrole derivative or a furan derivative.

16. The polymer as claimed in claim 13, wherein least 1% and not more than 70% of one or more of the structural units of the formulae (III) to (XIX),

Formula (III)

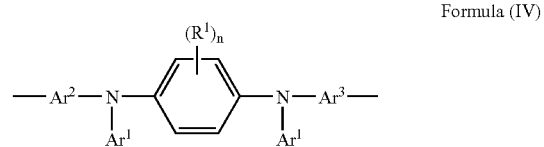
Formula (IV)

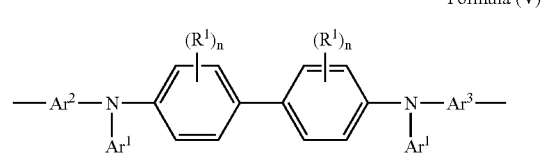
Formula (V)

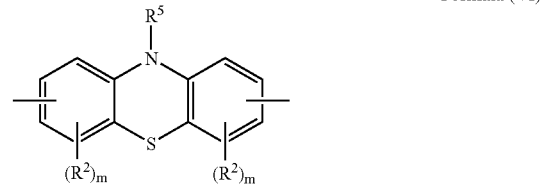
Formula (VI)

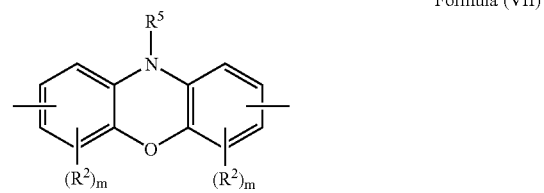
Formula (VII)

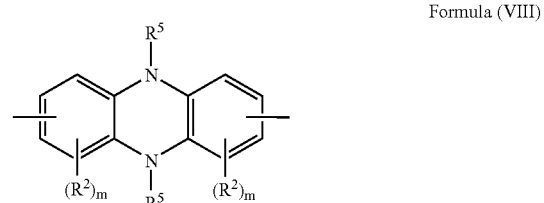
Formula (VIII)

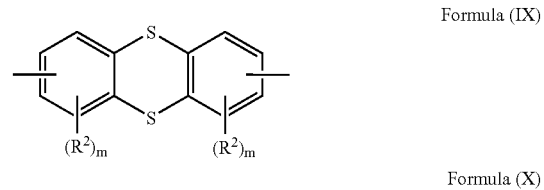
Formula (IX)

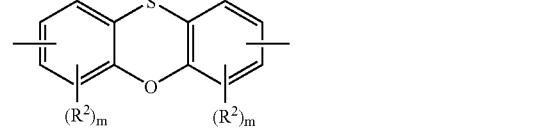
Formula (X)

-continued

Formula (XI)
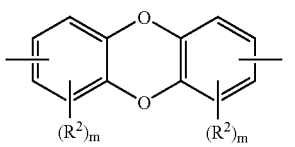

Formula (XII)
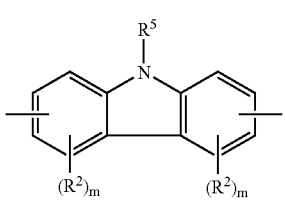

Formula (XIII)
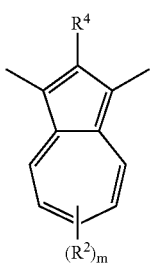

Formula (XIV)
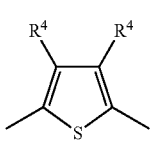

Formula (XV)
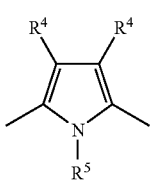

Formula (XVI)
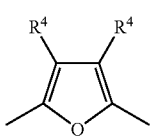

Formula (XVII)
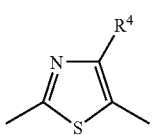

Formula (XVIII)
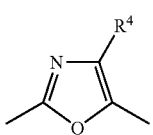

Formula (XIX)
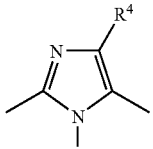

$Ar^1$, $Ar^2$ and $A^3$ are identical or different on each occurrence and are aromatic or heteroaromatic hydrocarbons which have from 2 to 40 carbon atoms and is optionally substituted by one or more nonaromatic radicals $R^1$, are present.

17. The polymer as claimed in claim 1, wherein said at least one further structural element has electron transport properties.

18. The polymer as claimed in claim 17, wherein at least one of the following structural elements pyridine derivatives, pyrimidine derivatives, pyridazine derivatives, pyrazine derivatives, oxadiazole derivatives, quinoline derivatives, quinoxaline derivatives or phenazine derivatives is present.

19. The polymer as claimed in claim 17, wherein at least 1% and not more than 70% of one or more of the structural units of the formulae (XX) to (XXX), Formula (XX)

Formula (XXI)

Formula (XXII)

(XXIII)

(XXIV)
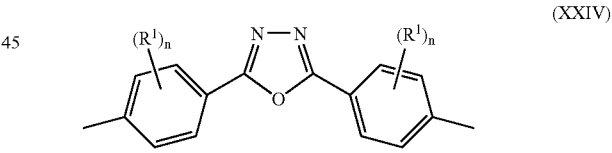

(XXV)
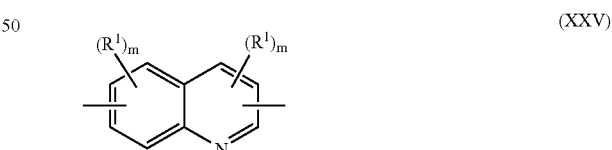

(XXVI)
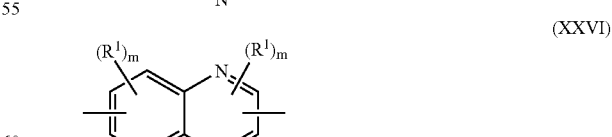

(XXVII)
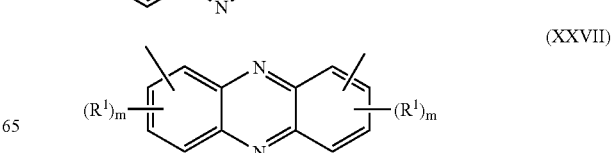

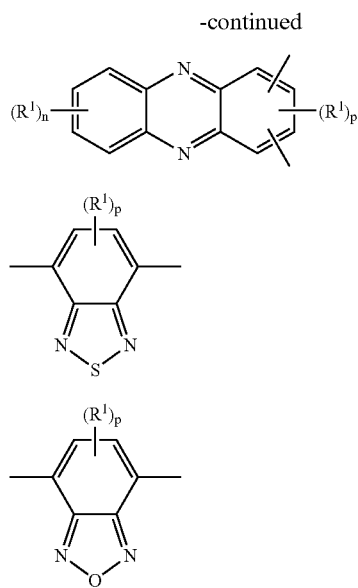
p is 0, 1 or 2,
are present.
20. The polymer as claimed in claim 1, wherein said at least one further structural element has electron transport properties and has hole transport properties.
21. The polymer as claimed in claim 20, wherein one or more structural elements of the formulae (III) to (XIX)
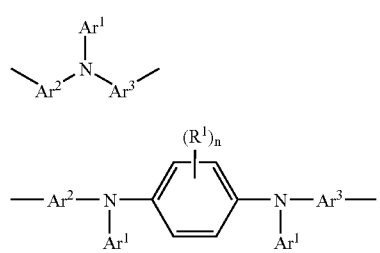
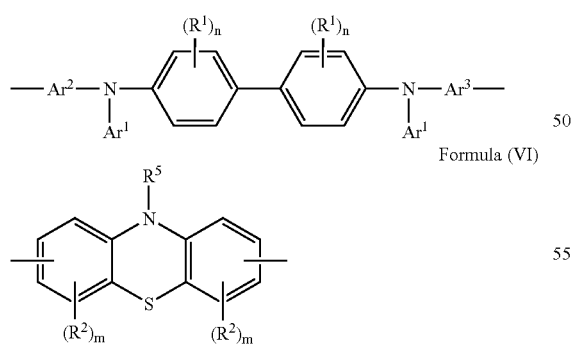
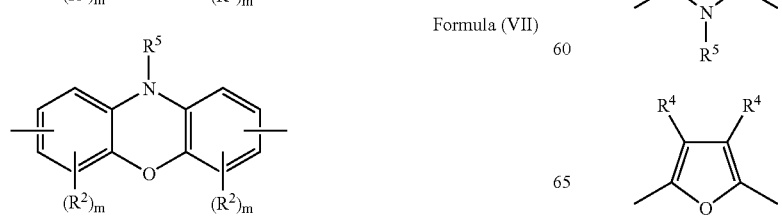

Formula (XVII)
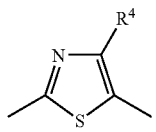

Formula (XVIII)
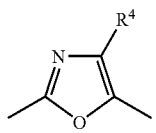

Formula (XIX)
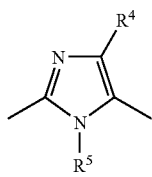

together with one or more structural elements of the formulae (XX) to (XXX)

Formula (XX)

Formula (XXI)

Formula (XXII)

Formula (XXIII)

Formula (XXIV)

Formula (XXV)

Formula (XXVI)

Formula (XXVII)
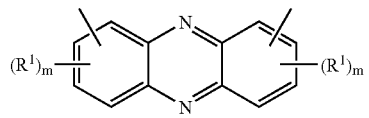

Formula (XXVIII)
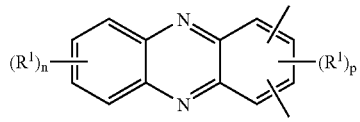

Formula (XXIX)
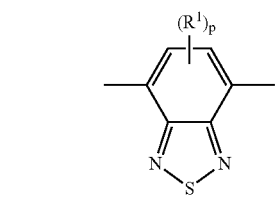

Formula (XXX)
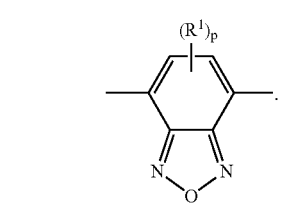

22. The polymer as claimed in claim 21, wherein the polymer further comprises one or more structural units of the formulae (XXXI) to (XXXXV), Formula (XXXI)
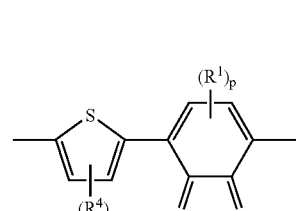

Formula (XXXII)
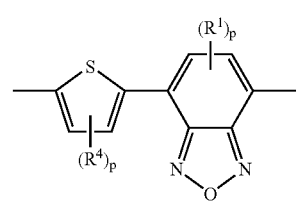

Formula (XXXIII)
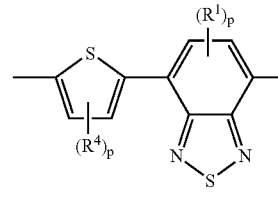

-continued

Formula (XXXIV)
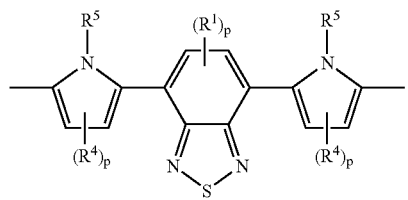

Formula (XXXV)
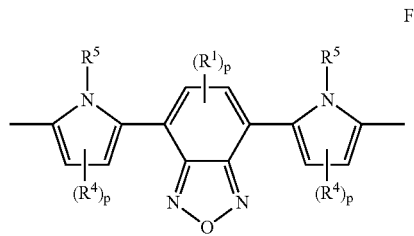

Formula (XXXVI)
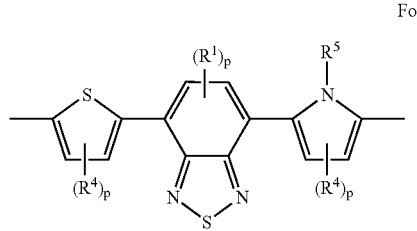

Formula (XXXVII)
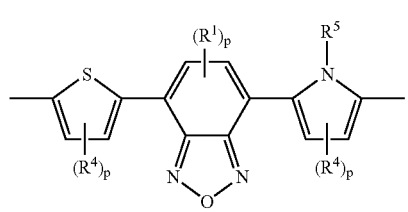

Formula (XXXVIII)
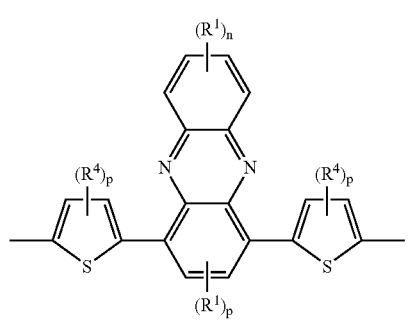

Formula (XXXIX)
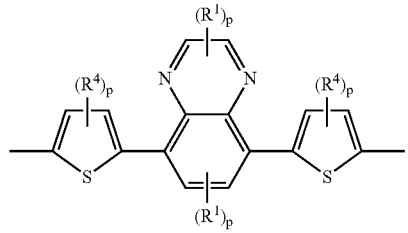

-continued

Formula (XXXX)
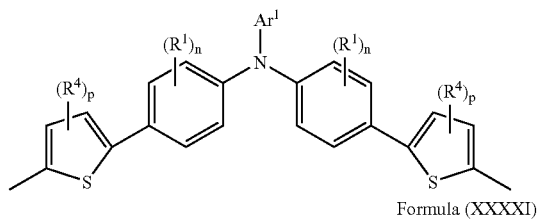

Formula (XXXXI)
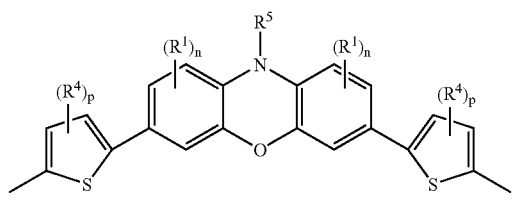

Formula (XXXXII)
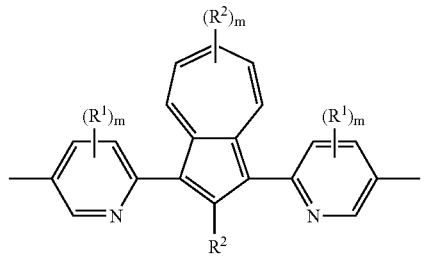

Formula (XXXXIII)
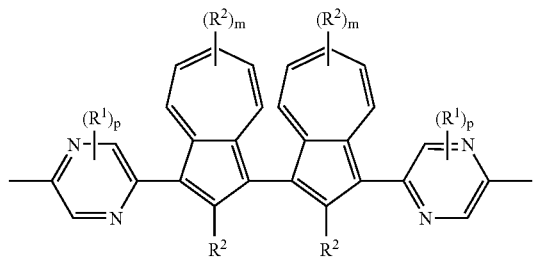

Formula (XXXXIV)
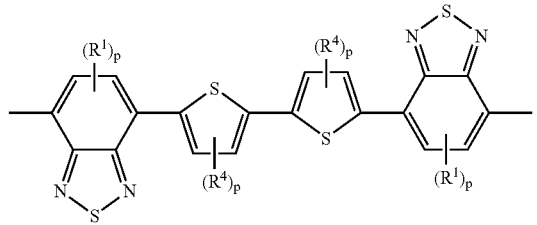

Formula (XXXXV)
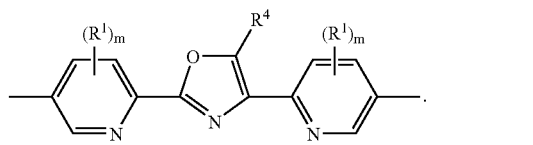

23. The polymer as claimed in claim 1, which further comprises at least one additional aromatic or other conjugated structure which has no influence or only little influence on the charge carrier mobilities.

24. The polymer as claimed in claim 23, wherein said aromatic structure has from 6 to 40 carbon atoms or stilbene or bisstyrylarylene derivatives which is optionally substituted by one or more nonaromatic radicals R¹.

25. The polymer as claimed in claim 23, wherein said aromatic structure is 1,4-phenylene, 1,4-naphthylene, 1,4- or 9,10-anthracenylene, 1,6- or 2,7- or 4,9-pyrene, 3,9- or 3,10-perylene, 2,7- or 3,6-phenanthrene, 4,4'-biphenylene, 4,4''-terphenylene, 4,4'-bi-1,1'-naphthylene, 4,4'-stilbene or 4,4''-bisstyrylarylene derivatives.

26. The polymer as claimed in claim 1, wherein organometallic complexes are incorporated into the main chain.

27. The polymer as claimed in claim 26, wherein said organometallic complexes are d transition metal complexes of the higher metals of the iron, cobalt and nickel triads.

28. The polymer as claimed in claim 27, wherein said transition metal complexes are complexes of ruthenium, osmium, rhodium, iridium, palladium or platinum.

29. The polymer as claimed in claim 26, which further comprises one or more of the structural units of the formulae (XXXXVI) to (XXXXIX), Formula (XXXXVI)

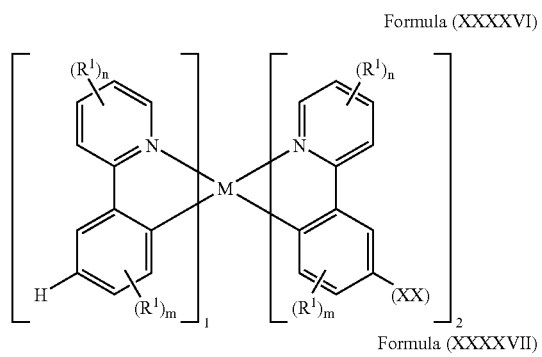

Formula (XXXXVII)

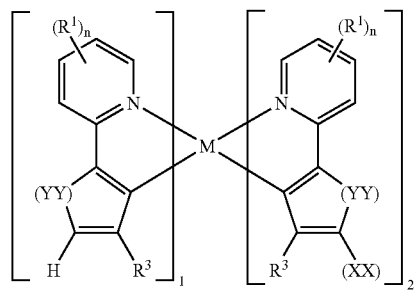

Formula (XXXXVIII)

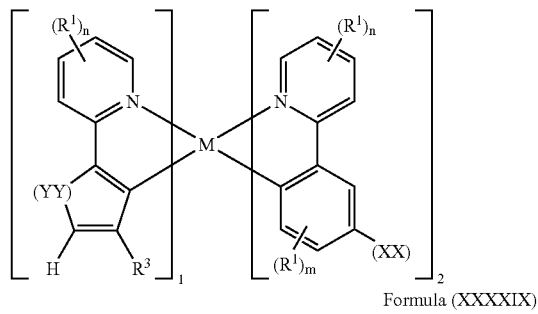

Formula (XXXXIX)

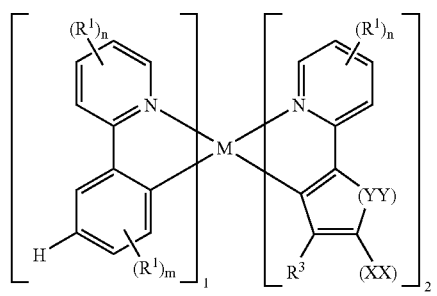

M is Rh or Ir,
XX is the point of linkage in the polymer, and
YY is identical or different on each occurrence and is O, S or Se.

30. An electroluminescence material which comprises one or more polymers as claimed in claim 1.

31. A PLED having one or more active layers, wherein at least one of these active layers comprises one or more polymers as claimed in claim 2.

32. An electronic component device comprising one or more polymers as claimed in claim 2.

33. An organic integrated circuit (O—IC), organic field effect transistor (OFET), organic thin film transistor (OTFT), organic solar cell (O—SC) or organic laser diode (O laser), which comprises one or more polymers as claimed in claim 1.

34. The polymer as claimed in claim 1, wherein the polymer has a $M_w$ from 56,000 to 750,000 g/mol and $M_n$ from 24,000 to 230,000 g/mol.

* * * * *

UNITED STATES PATENT AND TRADEMARK OFFICE
CERTIFICATE OF CORRECTION

PATENT NO. : 7,288,617 B2
APPLICATION NO. : 10/472736
DATED : October 30, 2007
INVENTOR(S) : Kevin Treacher et al.

It is certified that error appears in the above-identified patent and that said Letters Patent is hereby corrected as shown below:

On the Title Page:

Item [75] In the Inventors:

"Kevin Treacher, Kelkeheim/Munster (DE)" should read -- Kevin Treacher, Northwich (GB) --.

"Heinrich Becker, Glashütten (DE)" should read -- Heinrich Becker, Engstein-Nuedergosbaun (DE) --.

"Philipp Stossel" should read -- Philipp Stoessel --.

"Aurelie Falcou, Mainz (DE)" should read -- Aurelie Falcou, Frankfurt (DE) --.

"Arne Busing" should read -- Arne Buesing --.

In the Claims:

In Claim 16, in column 39 and line 66, "$Ar^1$, $Ar^2$ and $A^3$" should read -- $Ar^1$, $Ar^2$ and $Ar^3$ --.

Signed and Sealed this

Eighteenth Day of March, 2008

JON W. DUDAS
*Director of the United States Patent and Trademark Office*